(12) United States Patent
Keller

(10) Patent No.: US 11,426,308 B2
(45) Date of Patent: *Aug. 30, 2022

(54) CAPSULOTOMY DEVICE

(71) Applicant: Centricity Vision, Inc., Fremont, CA (US)

(72) Inventor: Christopher Guild Keller, El Cerrito, CA (US)

(73) Assignee: CENTRICITY VISION, INC., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/917,682

(22) Filed: Jun. 30, 2020

(65) Prior Publication Data

US 2020/0330271 A1 Oct. 22, 2020

Related U.S. Application Data

(63) Continuation of application No. 16/236,346, filed on Dec. 29, 2018, now Pat. No. 10,736,777, which is a
(Continued)

(51) Int. Cl.
*A61B 18/14* (2006.01)
*A61F 9/007* (2006.01)
(Continued)

(52) U.S. Cl.
CPC .......... *A61F 9/00754* (2013.01); *A61B 18/14* (2013.01); *A61B 18/1402* (2013.01);
(Continued)

(58) Field of Classification Search
CPC ................ A61B 18/14; A61B 18/1402; A61B 2018/00291; A61B 2018/00321;
(Continued)

(56) References Cited

U.S. PATENT DOCUMENTS

| 8,162,931 B2 | 4/2012 | Ben-Nun |
| 8,235,978 B2 | 8/2012 | Ben-Nun |
| 8,657,813 B2 | 2/2014 | Ben-Nun et al. |
| 8,702,698 B2 | 4/2014 | Keller |

(Continued)

FOREIGN PATENT DOCUMENTS

| CN | 102026600 A | 4/2011 |
| JP | 2005-500893 A | 1/2005 |

(Continued)

OTHER PUBLICATIONS

Chinese Second Office Action, Chinese Application No. 2012800638755, dated Nov. 3, 2015, 6 pages.

(Continued)

*Primary Examiner* — Michael F Peffley
(74) *Attorney, Agent, or Firm* — Fenwick & West LLP

(57) ABSTRACT

A surgical device and procedure are provided for smoothly and easily accessing tissue to perform microsurgery, including a capsulotomy of a lens capsule of an eye. The device includes a handpiece with a tip for insertion into an incision in the cornea of the eye. A sliding element is disposed within the handpiece and a suction cup is mounted to the sliding element. The sliding element can be translated to move the suction cup into and out of the handpiece. A compression mechanism associated with the suction cup and the handpiece compresses the suction cup for deployment through the tip of the handpiece. The suction cup can expand inside the anterior chamber into a cutting position on the lens capsule. A cutting element mounted to the suction cup is used to cut a portion of the lens capsule and to remove the portion from the eye. The cutting element may be mounted to a cutting element support structure in a way that prevents heating of the device.

19 Claims, 31 Drawing Sheets

Related U.S. Application Data continuation of application No. 14/353,220, filed as application No. PCT/US2012/061361 on Oct. 22, 2012, now Pat. No. 10,206,816.

(60) Provisional application No. 61/550,111, filed on Oct. 21, 2011.

(51) Int. Cl.
*A61F 9/00* (2006.01)
*A61B 18/00* (2006.01)

(52) U.S. Cl.
CPC .. *A61F 9/0017* (2013.01); *A61B 2018/00291* (2013.01); *A61B 2018/00321* (2013.01); *A61B 2018/00601* (2013.01); *A61B 2018/1407* (2013.01)

(58) Field of Classification Search
CPC ... A61B 2018/00601; A61B 2018/1407; A61F 9/0017; A61F 9/00754
See application file for complete search history.

(56) References Cited

U.S. PATENT DOCUMENTS

| | | | |
|---|---|---|---|
| 2003/0233091 A1 | 12/2003 | Whayne et al. | |
| 2004/0260254 A1* | 12/2004 | Neilson | A61F 9/0017 604/297 |
| 2006/0086608 A1 | 4/2006 | Kwak et al. | |
| 2007/0191862 A1* | 8/2007 | Ellis | A61F 9/00754 606/107 |
| 2010/0179544 A1 | 7/2010 | Boukhny et al. | |
| 2010/0312232 A1 | 12/2010 | Jia et al. | |
| 2011/0071524 A1* | 3/2011 | Keller | A61B 18/085 606/45 |
| 2011/0118734 A1 | 5/2011 | Auld et al. | |
| 2013/0197548 A1* | 8/2013 | Keller | A61B 17/32 606/166 |
| 2014/0074088 A1 | 3/2014 | Ben Nun et al. | |

FOREIGN PATENT DOCUMENTS

| | | |
|---|---|---|
| JP | 2007-505713 A | 3/2007 |
| JP | 2008-155038 A | 7/2008 |
| WO | WO 1999/060936 A1 | 12/1999 |
| WO | WO 2001/056519 A1 | 8/2001 |
| WO | WO 2002/043632 A1 | 6/2002 |
| WO | WO 2003/022191 A1 | 3/2003 |
| WO | WO 2004/01 7877 A1 | 3/2004 |
| WO | WO 2005/082302 A1 | 9/2005 |
| WO | WO 2007/120775 A2 | 10/2007 |
| WO | WO 2009/140414 A1 | 11/2009 |
| WO | WO 2013/022854 A1 | 2/2013 |

OTHER PUBLICATIONS

European Patent Office, Search Report and Opinion, European Patent Application No. 12847125.7, dated Apr. 24, 2015, seven pages.

Japanese Office Action, Japanese Application No. 2014-537364, dated Sep. 6, 2016, 12 pages.

Japanese Office Action, Japanese Application No. 2017-057834, dated Feb. 20, 2018, 9 pages.

PCT International Search Report and Written Opinion, PCT Application No. PCT/US2012/61361, Jan. 9, 2013, 11 pages.

PCT International Search Report and Written Opinion, PCT/US2012/061361, Jan. 9, 2013, 18 Pages.

State Intellectual Property Office of the People's Republic of China, First Office Action, Chinese Patent Application No. 2012800638755, Feb. 28, 2015, 15 pages.

United States Office Action, U.S. Appl. No. 14/353,220, filed Apr. 19, 2018, 6 pages.

United States Office Action, U.S. Appl. No. 14/353,220, filed Aug. 22, 2017, 10 pages.

United States Office Action, U.S. Appl. No. 16/236,346, filed Feb. 21, 2020, 11 pages.

* cited by examiner

301

CAPSULOTOMY DEVICE

CROSS-REFERENCE TO RELATED APPLICATIONS

This application is a continuation of U.S. application Ser. No. 16/236,346 filed on Dec. 29, 2018, now U.S. Pat. No. 10,736,777, which is a continuation of U.S. application Ser. No. 14/353,220, with a 371(c) date of Apr. 21, 2014, now U.S. Pat. No. 10,206,816, issued on Feb. 19, 2019, which is a National Stage Entry of International Application No. PCT/US2012/061361 filed on Oct. 22, 2012, which claims the benefit of U.S. Provisional Patent Application No. 61/550,111, filed Oct. 21, 2011, each of which is incorporated herein by reference in its entirety for all purposes.

STATEMENT REGARDING FEDERALLY SPONSORED RESEARCH OR DEVELOPMENT

This invention was made with government support under Grant Numbers 3R44EY021023-0351, 5R44EY021023-03, 1R43EY021023-01A1, 2R44EY021023-04, and 2R44EY021023-02, awarded by the National Institutes of Health. The government has certain rights in the invention.

BACKGROUND

This invention pertains in general to microsurgery of tissue, and more specifically to procedures and devices for accessing a tissue through another tissue layer, to cut or otherwise manipulate that tissue. For example, the procedures and devices can be used to deliver an ophthalmic surgical device through the cornea to the anterior lens capsule membrane in the anterior chamber of an eye.

Lens cataract is the leading cause of blindness worldwide and surgical treatment by cataract removal is the treatment of choice. A cataract is a clouding that develops in the lens of the eye or in its envelope. The creation of areas of opacity in the lens obstructs the passage of light. The lens of the eye is supposed to be transparent. If the lens develops opaque areas, as in a cataract, the lens must be surgically removed. If no lens is present in the eye, corrective glasses are required to focus an image on the retina. The lens, however, can be replaced with an artificial intraocular lens (IOL) to provide better vision after cataract removal. There may also be other reasons such as presbyopia to replace a lens that is not serving its functions appropriately.

The removal of the lens for replacement with an IOL is a surgical procedure that requires substantial precision. The lens is completely enclosed by a membrane called the lens capsule, so the surgeon must first cut through the capsule to access the lens. It is important to cut the capsule in just the right way. If the lens capsule has been cut correctly, and not damaged during the cataract removal, then it can be used to hold an IOL. The implantation of an IOL requires the creation of an opening in the lens capsule that is precisely centered, sized, and shaped for implant stability and for optimal IOL function. The matching of the lens capsule opening size to the peripheral margins of the IOL is critical. The goal of the surgeon is to create a perfectly circular (e.g., 5.5+/−0.1 mm diameter) hole in the capsular membrane (i.e., the lens capsule) that encapsulates the lens, centered on the optical axis of the eye, with no tears or defects in the edge of the hole. Tears or defects on the edge of the hole make the capsule very weak and vulnerable to losing the ability to hold the IOL properly. Different IOL designs may require a different diameter for the hole (e.g., ranging from 4.5+/−0.1 mm to 6.0+/−0.1 mm), but whatever the prescribed diameter is, the accuracy of the surgeon in actually achieving it is very important for proper outcome of the cataract surgery. This is especially true of IOLs intended to perform complex optical and focusing functions.

Creating an opening in the lens capsule with this required level of precision is a difficult task for a surgeon controlling and guiding conventional handheld cutting instruments and attempting to trace a precise circular route on the lens capsule. Currently, to perform a capsulotomy (the creation of an opening in the lens capsule), the surgeon typically manually creates a small tear in the anterior region of the lens capsule. With great caution, the surgeon then uses a small forceps to try to extend the edge of the tear so as to follow a circular path of the specified diameter and centered on the optic axis of the eye. In practice, it often happens that the hole does not end up circular, or the correct diameter, or centered on the optic axis. There can also be radial tears in the edge of the hole that greatly weaken the capsule. As a result of any of these errors, the capsule may not be able to hold the IOL properly, and optimal visual outcome cannot be achieved.

In addition to the difficulties faced by the surgeon in accessing the lens by performing a precise capsulotomy of the lens capsule, the surgeon must also be able to access the lens capsule itself. The lens is positioned in the anterior chamber of the eye. To access the lens capsule, the surgeon must create an incision in the cornea and carefully insert the capsulotomy instruments through this incision. The same requirement exists in a number of microsurgery procedures in which an incision in a first layer of tissue must be passed through before a second layer of tissue, behind or beneath that first layer, can be accessed. For the surgeon to maneuver the microsurgery instruments through the corneal incision, the incision must be of sufficient size to accommodate these instruments. However, the larger the incision, the greater the risk of infection, of corneal distortion, astigmatism, and of other complications. Microsurgery instruments commonly are not compact enough or are not sufficiently streamlined in shape, making it difficult for the surgeon to minimize the incision size or possibly risking tears or other damage at the incision site. Cutting elements or other sharp components are sometimes exposed during insertion, requiring the surgeon to be very precise and creating further risk of collateral damage to tissue when inserting the instrument through the incision. Further, this insertion often requires multiple steps and sometimes complex maneuvering of instruments by the surgeon, leaving little room for error. Once inserted, instruments are often not easily manipulated and the surgeon may be forced to handle and move multiple separate pieces in a small space. Any of these problems can make it very difficult for a surgeon to access a second layer of tissue behind a first layer, particularly when the second layer is tissue in a very small area, such as within the eye.

Given the drawbacks of existing treatment devices/procedures for accessing tissue, such as the lens capsule, to perform surgery, improved techniques and devices for performing microsurgery are needed.

SUMMARY

Embodiments of the invention include devices and methods for accessing a lens capsule through a cornea of an eye, for performing a capsulotomy in the eye. In one embodiment, provided herein is a capsulotomy device for accessing a lens capsule through a cornea of an eye, the device comprising: an elastomeric structure; a support structure mounted to the elastomeric structure; and a cutting element extending from the support structure that is mounted to the elastomeric structure, wherein the cutting element and the elastomeric structure are not in physical contact.

In an embodiment, the cutting element is an electrode, and the device comprises one or more electrical elements for delivering current to an electrical lead connected to the electrode to heat the electrode for excising a portion of tissue of the lens capsule. In some embodiments, the electrode is circular. In certain embodiments, the electrode comprises a continuous element and the device further comprises a first and second connecting trace connecting the electrical lead to the electrode, wherein the connecting traces are positioned on opposite sides of the electrode to allow current to travel in two opposite directions for conducting current uniformly around the portion of the tissue to be severed.

In an embodiment, the elastomeric structure is a suction cup. In a further embodiment, the device comprises one or more suction elements connected to the suction cup for applying suction within the suction cup. In an embodiment, the suction cup further comprises a flared skirt extending from an edge of the suction cup for securing the suction cup against the lens capsule to form a vacuum seal.

In some embodiments, the support structure comprises a series of openings along the length of the support structure. In one aspect of the embodiment, the support structure comprises a plurality of tabs. In a further aspect of the embodiment, the support structure comprises a plurality of tabs so that the portion of the support structure in contact with the elastomeric structure does not form a complete circuit for current flow.

In certain embodiments, the cutting element is positioned on one side of the support structure. In other embodiments, the cutting element is positioned on at least two sides of the support structure. In one embodiment, the cutting element comprises at least two electrodes. In other embodiments, the cutting element is positioned on at least three sides of the support structure.

In an embodiment, the device comprises a stem attached to the elastomeric structure to provide support between a handle and the elastomeric structure and attached structures. In some embodiments, the stem comprises electrically conductive elements for providing current to the cutting element. In some embodiments, the stem comprises a tube for applying suction between the elastomeric structure and the lens capsule. In an embodiment, the stem comprises a support arm. In a further embodiment, the support arm is electrically conductive, and wherein the support arm is electrically connected to the cutting element. In some embodiments, the support arm is tube-shaped to apply suction between the elastomeric structure and the lens capsule.

Also provided herein, in certain embodiments, is a capsulotomy device for accessing a lens capsule through a cornea of an eye, the device comprising: an elastomeric structure; and a support structure mounted to the elastomeric structure, the support structure comprising a plurality of openings along the length of the top of the support structure wherein the top of the support structure is attached to the elastomeric structure, the support structure comprising a cutting element segment along the length of the bottom of the support structure.

In some embodiments, the support structure comprises at least two materials, wherein the material comprising the cutting element segment is more conductive than the material of the support structure attached to the elastomeric material. In certain embodiments, the support structure and the cutting element segment are continuous and made from the same material. In an embodiment, the support structure comprises a plurality of tabs attached to the elastomeric structure and wherein the support structure connects the elastomeric structure to the cutting element segment. In some embodiments, the support structure is discontinuous to inhibit current flow around the path of the support structure attached to the elastomeric structure.

In some embodiments, the support structure is attached to a support arm extending into a stem of the device. In an embodiment, the support arm is conductive to allow current to flow along the support arm from the stem to the cutting element segment. In certain embodiments, the support arm comprises u-shaped elements extending from the support structure, and wherein the u-shaped elements comprise tubes for applying suction between the elastomeric structure and the lens capsule. In one embodiment, the support arm is tube-shaped for applying suction between the elastomeric structure and the lens capsule.

In one embodiment, provided herein is a method for performing a capsulotomy of a lens capsule of an eye, the method comprising: contacting the lens capsule with a cutting element, wherein the cutting element extends from a support structure, wherein the support structure is mounted to an elastomeric structure, and wherein the cutting element and the elastomeric structure are not in physical contact; and applying energy to the lens capsule along the cutting element during the application of stress, resulting in the cutting of a portion of the lens capsule along the cutting element.

In one embodiment, the cutting element is an electrode. In another embodiment, the electrode is circular. In an embodiment, the cutting element is in uniform contact with the lens capsule.

In some embodiments, applying energy comprises applying an electric pulse or a series of pulses to the electrode. In other embodiments, applying energy comprises applying resistive heating along the cutting element.

In certain embodiments, the elastomeric structure is a suction cup. In an embodiment, the method comprises applying a suction to the suction cup for securing the suction cup to the lens capsule of the eye after placing the cutting element inside the anterior chamber of the eye into a cutting position on the lens capsule, the suction pulling tissue of the lens capsule against the cutting element. In some embodiments, the method comprises applying a suction to the suction cup, the suction securing a flared skirt of the suction cup against the lens capsule and pulling tissue against the cutting element.

In an embodiment, provided herein is a method for performing a capsulotomy of a lens capsule of an eye, the method comprising: contacting the lens capsule with a cutting element segment, wherein the cutting element segment extends from the bottom of a support structure along its length, wherein the top of the support structure is mounted to an elastomeric structure, and wherein the length of the top of the support structure comprises a plurality of openings to inhibit the flow of current at the top of the support structure attached to the elastomeric structure; and applying energy to the lens capsule along the cutting element during the application of stress, resulting in the cutting of a portion of the lens capsule along the cutting element.

In some embodiments, provided herein is a device for accessing a second layer of tissue behind a first layer of tissue for performing microsurgery or therapeutic work, the device comprising: an operational element associated with the elastomeric structure for engaging in microsurgery or therapeutic work on the second layer of tissue, wherein the operational element is attached to a support structure.

In an embodiment, the operational element comprises a cutting element mounted to the elastomeric structure for cutting a portion of the second layer of tissue. In certain embodiments, the cutting element is an electrode.

Also provided herein, in some embodiments, is a method for accessing a second layer of tissue behind a first layer of tissue for performing microsurgery or therapeutic work, the method comprising: contacting the second layer of tissue with a cutting element, wherein the cutting element is mounted to an elastomeric structure, and wherein the cutting element is attached to a support structure; and engaging in microsurgery or therapeutic work on a portion of the second layer of tissue.

In some embodiments, engaging in microsurgery or therapeutic work further comprises cutting a portion of the second layer of tissue with a cutting element mounted to the elastomeric structure.

These and other embodiments of the invention are further described in the Figures, Description, Examples and Claims, herein.

Figure 1:
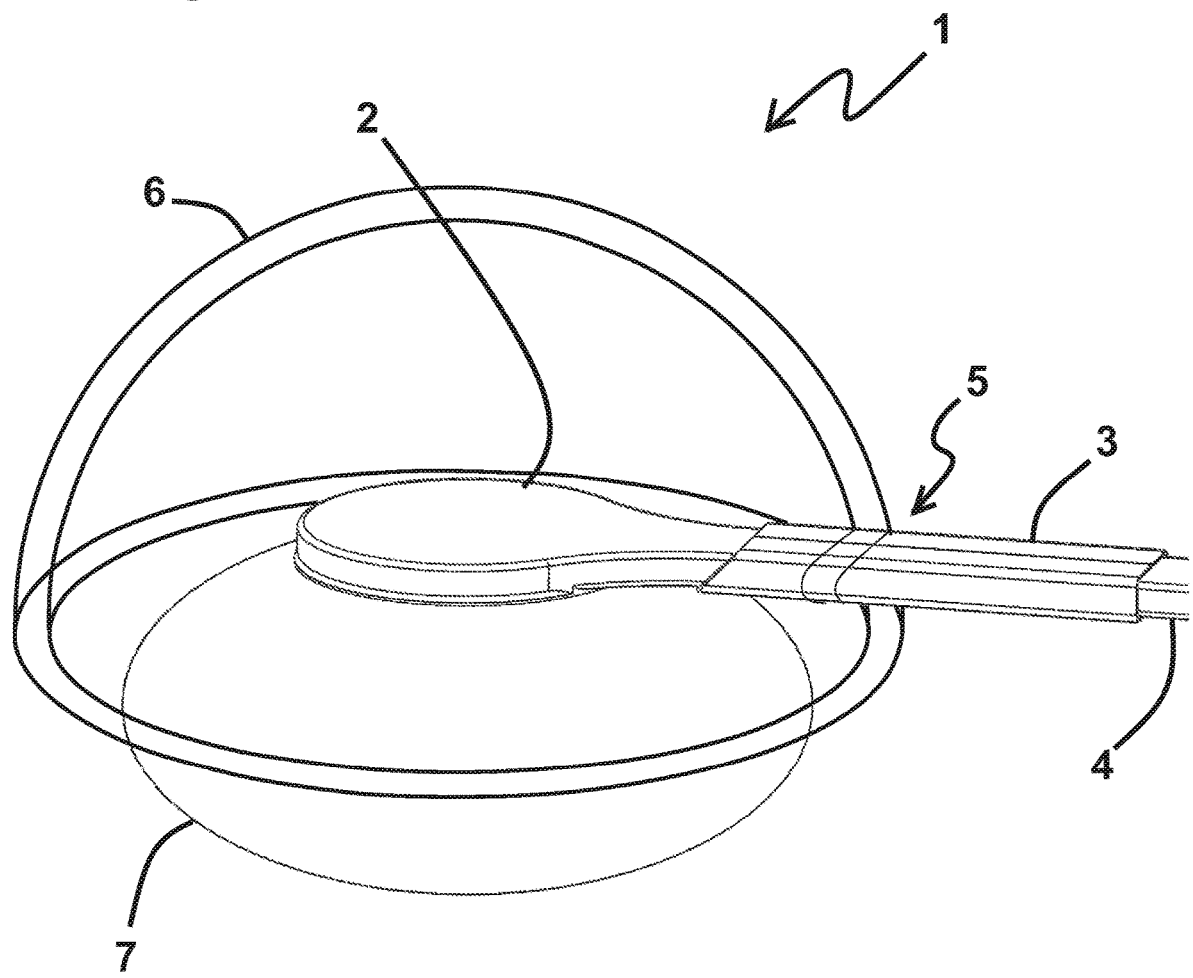
FIG. 1 is a side perspective view of the microsurgery/capsulotomy device with the suction cup deployed and in contact with the lens capsule of the eye, according to an embodiment of the invention.

The figures depict an embodiment of the present invention for purposes of illustration only. One skilled in the art will readily recognize from the following description that alternative embodiments of the structures and methods illustrated herein may be employed without departing from the principles of the invention described herein.

DETAILED DESCRIPTION

Embodiments of the invention are described herein in the context of a lens capsule surgery in which a portion of the anterior surface of a lens capsule is cut. This technique may be used for performing treatment for cataracts in which all or a portion of a lens located within the lens capsule is removed from the eye. The procedure may also be used to create an access hole in the lens capsule through which to implant an artificial lens (e.g., an intraocular lens, or IOL) within the lens capsule. Though often described herein in terms of performing lens capsule surgery, the devices and procedures are not limited to lens capsule surgery, but can also be useful in other treatments of the eye, such as a corneal surgery, treatments for glaucoma, microfenestration of the optic nerve, surgeries involving decemet's membrane, among others. Furthermore, the devices and procedures may also be useful in the delivery of pharmacologic, biologic, and chemical entities and therapeutics. The devices and procedures can also be used to deliver fluids in addition to suction, and the delivery can be specifically localized (e.g., by the suction cup) limiting exposure only to desired tissues. In addition, the devices and procedures may be useful for industrial applications or performing other medical procedures outside of the eye, such as procedures involving excision of delicate membranes or tissue structures, fenestration of brain dura, vascular tissues and others. The devices and procedures can also be used outside of the body, on tissue excised and separate from the body, for industrial applications, etc. In these other types of applications, the procedures and devices function generally in the same manner as described regarding the lens capsule surgery, though the components may be differently arranged, sized, shaped to accommodate different tissue.

The term "pulse" as used herein refers to the length of time the electrical pulse is on, for example 100 microseconds. If the pulse is a DC pulse the current is going in only one direction (but amplitude may be changing) during the entire 100 microseconds. If it is an AC pulse the current reverses direction during the 100 microseconds. If the AC frequency is in the RF or in the microwave range there will be many cycles during the 100 microsecond pulse. The frequency and amplitude may change or slow during the 100 microseconds and that kind of pulse is called a "chirp"), and the current path may go around the ring of metal, or may go from the ring through tissue to a return electrode.

The term "elastomeric structure" refers to a bendable/foldable structure that can provide an air-tight seal between the edges of the elastomeric structure and tissue. In one embodiment, the elastomeric structure is functionally linked to a cutting element, the elastomeric structure providing a fluidic seal between the elastomeric structure and the tissue, allowing a vacuum pressure applied between the elastomeric structure and the tissue to result in a pressure that presses the cutting element against the tissue.

The term "cutting element" refers to an element designed to cut tissue through application of pressure and/or electrical current. The cutting element can be made from various materials. In one embodiment, the cutting element refers to an "electrode" (e.g., an "electrode segment"). The metallic components of the electrode can be made by electroforming of suitable metals such as nickel, gold, steel, copper, platinum, iridium, etc. Connections between the electrode and leads in the stem can be made by electroplating, or welding. Typically, for electrical cutting elements, the material for the cutting element is electrically conductive, and for mechanical cutting elements, the material is hard enough to pierce the membrane. For both electrical and mechanical cutting elements, the material is also generally elastic enough to return to its prior shape after being squeezed to get through the tissue incision, or soft enough to be pushed back into circular shape by the polymeric support ring and/or by the suction cup in which it is mounted. For example, for an electrical cutting element, the materials can include those made by photochemical etching, such as spring steel, stainless steel, titanium nickel alloy, graphite, nitinol (NiTi alloy "memory metal"), nickel, nickel-chrome alloy, tungsten, molybdenum, or any other material that will allow the element to return to its prior shape. Other materials for electrical cutting elements include electrically conductive elastomers, including elastomers (e.g., silicone or polyurethane) mixed with appropriately shaped conductive particles (e.g., silver, gold, graphite, or copper) that can establish contact with each other and continue to be in contact with each other for the duration of the electrical discharge. An additional example of a material for electrical cutting elements includes a compliant mesh of very fine wires (e.g., diameter of about 1 or 2 microns) that can be anchored in the elastomeric support ring to make the conductive element. As a further example, materials can be used for electrical cutting elements that are made by sputtering metal onto a polymeric support, such as high conductivity metals (e.g., gold, aluminum, copper, etc.), which can be used to make very thin (e.g., 1 micron) elements with resistance within the usable range (e.g., 1 to 10 ohms) deposited by RF plasma sputtering.

Materials used for mechanical cutting elements can include photochemically etched metal (e.g., stainless steel), or a relatively hard plastic (e.g., phenolic), among others. Discrete micro teeth could be etched from single crystal silicon. Photochemical etching can used to make cutting elements that have a thickness of, for example, 25 microns, or 12.5 microns, or 5 microns, and so forth.

The term "conductor" refers to a substance or medium that conducts an electric charge. Whenever "gold" is mentioned herein as an element used as a conductor, it is to be understood that alternative materials suitable as good conductors may also be used, including by way of example and not limitation, Pt, Cu, Ni, Ta, Ir, Re, and their alloys. A conductor may refer to a heating element. Heating elements may be made from a large set of suitable conductive materials, including by way of example and not limitation: gold, Pt, Ta, Ir, Re, Al, Ag, and their alloys (e.g., Ta/Al, Pt/Ir, etc.), tantalum nitride, titanium nitride, carbides that are doped to be conductive, etc.

The term "insulator" refers to any material or object that does not easily allow heat or electricity to pass through it, e.g., a material with a very low electrical conductivity or thermal conductivity or something made of such a material. An insulator may include, by way of example and not limitation, polymers (e.g., kapton, silicone, etc.), glass (e.g., chemically strengthened glass), ceramics (e.g., tantalum oxide, titanium oxide, nonconductive oxides, nitrides, and oxynitrides, etc.).

The term "cutting element support structure," "electrode support structure," or "support structure" refers to a structure used to extend from and/or attach to and support a cutting element or electrode. In some embodiments, the electrode support structure is elastomeric. In some embodiments, the support structure is made of nitinol. Whenever nitinol is mentioned as a material used for mechanical support element such as an electrode support structure, it is to be understood that any suitable elastic material may be substituted, by way of example and not limitation: chemically strengthened glass, Hi Ten steel, stainless steel, polymer, Kapton, etc. In some embodiments, the electrode support comprises a series of tabs that provide an interface between the electrode and another structure, e.g., potting material or an elastomeric structure (e.g., a suction cup). In some embodiments, the cutting element support structure is mechanically separate from, but attached to, the cutting element. In other embodiments, the cutting element support structure is an extension of the cutting element, e.g., an extension of a conductive electrode, wherein the electrode support structure segment is less conductive and extends from the support structure. In other embodiments, the cutting element support structure is an extension of the cutting element made from the same material as each other, and wherein the cutting element support structure has notches to prevent flow of current around the cutting element support structure.

Microsurgery/Capsulotomy Device

A problem solved by this invention is how to perform a manual capsulotomy without inadvertently tearing tissue outside of the desired circular path. Using the present invention, the tear will follow the location of the thermally weakened material, which is defined by an electrode (e.g., a circular electrode). The tear will not run off into the stronger cold material. In one embodiment, the invention controls both the stresses in the membrane and the strength of the membrane at the exact circular path of interest, so undesired processes cannot occur.

In one embodiment, the microsurgery/capsulotomy device described herein uses suction force to contact a capsular membrane with the edge of a circular metal electrode, thereby establishing a state of uniform, circular contact between the electrode and the lens capsule, exactly where cutting is desired on the membrane, e.g., a circle on the capsular membrane. A short burst of electrical energy may then be passed through the electrode to cause stress along the electrode's contact with the membrane and complete the cut of the membrane along the electrode. The duration of the electrical pulse is less than 10 milliseconds (preferably about 10 to 100 microseconds or less) so that only a small volume of tissue is heated by it. The nature of the pulse may be DC, or AC (radio waves e.g., 1 MHz, or microwaves e.g., 2.4 GHz).

In another embodiment, a circular metal electrode, without suction cup, is carefully placed into uniform circular contact with the lens capsule to effect cutting in the same manner.

In one embodiment, described herein is a microsurgery/capsulotomy device comprising a circular electrode supported by a mechanically elastic electrode support structure. The electrode is made from a conductive metal, e.g., by way of example and not limitation: gold, platinum, copper, nickel, tantalum, iridium, rhenium, and their alloys. The mechanically elastic electrode support structure is made from an elastic material, e.g., by way of example and not limitation: nitinol (e.g., superelastic nitinol), chemically strengthened glass, Hi Ten steel, stainless steel, polymer, Kapton, etc. In this embodiment, where the mechanically elastic electrode support structure is made from an elastic material, it may be deformed to allow the microsurgery/capsulotomy device to be inserted through a small corneal incision, and then expanded back to its original shape within the anterior chamber of the eye. In one embodiment, the microsurgery/capsulotomy device further comprises an elastomeric structure (e.g., a suction cup), which attaches to the lens capsule. A suction force then will pull the capsular membrane in close contact with the electrode, where an electrical current lasting less than 0.0005 seconds (and preferably less than 0.0001 seconds) results in cutting the membrane. In some embodiments, the excised circular patch may be sucked out by a suction tube of the device. In other embodiments, the excised circular patch may be removed from the eye by sticking to the roof of the suction cup. These embodiments are described in more detail below.

In several embodiments of the invention, high temperatures generated from the current traveling to and through the electrode do not reach the elastomeric structure. This prevents outgassing caused by the heating of the device. In one embodiment, this is accomplished by placing a high conductivity circuit as a separate cutting element directly onto a cutting element support structure. The current will preferentially flow in through the cutting element and the support structure will not generate a lot of heat. Thus, the elastomeric structure will not reach a high temperature. In another embodiment, an insulating layer (i.e., an insulator) is placed between the support structure and the cutting element. In this case, the cutting element may be the same material or a different material than the support structure. In another embodiment, the support structure provides both a supporting function and its edge provides the cutting function (i.e., one structure serves both functions). In one aspect of this embodiment, the top portion of the support structure (where it is in contact with the elastomeric structure) has cutouts that prevent the current from flowing in a circuit around the top of the support structure. The bottom of the support structure has no cutouts, and thus can act as a cutting element (e.g., an electrode) with current flowing in a continuous path around the cutting element and generating the necessary heating for capsule cutting. In this case, a cutout is any modification to the support structure that inhibits current flow around the portion of the support structure attached to the elastomeric structure. These cutouts may result in 'tabs' that can be pointed radially into the center of the elastomeric structure, or remain aligned circumferentially.

FIG. 1 is a side perspective view of the microsurgery/capsulotomy device 1 in use in the eye. The relevant parts of the eye shown are the cornea 6 and the surface of the lens capsule 7. In the device, there is an elastomeric suction cup 2 that is held by suction force onto the lens capsule. The suction cup is attached to a stem 4 that contains tubing for suction, and electrical conductors for electrical currents. Within the suction cup is an electrode that confronts the capsule. The device is slid through an inserter 3 that has been pushed through a previously made incision 5 in the cornea.

Steps in a method of using the microsurgery capsulotomy device according to an embodiment of the invention are described below:

1. Visco (or other lubricating material) is applied to the suction cup 2 to act as a lubricant.

2. The suction cup and electrode are compressed (in a compression tool) to fit within the inserter (note that FIG. 1 does not show the handpiece structure (described later) to which the inserter is attached and through which the stem slides).
3. The suction cup and electrode are slid into the inserter.
4. A corneal incision 5 is made (using a separate ophthalmic tool).
5. The inserter 3 is pushed through the corneal incision.
6. The suction cup, electrode, and stem are made to slide out of the inserter to enter the eye.
7. After the suction cup enters the anterior chamber of the eye, it returns to its circular shape.
8. The surgeon positions the center of the circular electrode over the optic axis of the eye.
9. Suction is applied.
10. Suction forces the suction cup and electrode against the lens capsule.
11. An electrical current is made to flow through the electrode to cut the capsule.
12. The suction is turned off
13. Optionally, there is a reverse flow of fluid injected between the suction cup and the lens capsule to break the grip of the suction cup.
14. The device and the excised patch of membrane are removed from the eye.

Note that after steps 1, 2, 3, 5, 6, 7, 8, and 9 the system controller may send a small test current through the electrode to measure its resistance. If the resistance is too low or too high, the system will alert the surgeon that the device is broken and needs to be replaced. The measurement of resistance can be made continuously if desired. The steps described above are just one example of such a method, but fewer or more steps could be used, the steps modified, or the steps spaced out in time, or the steps can be reordered, as desired (the same is true for other methods/listings of steps described in this application).

Figure 2:
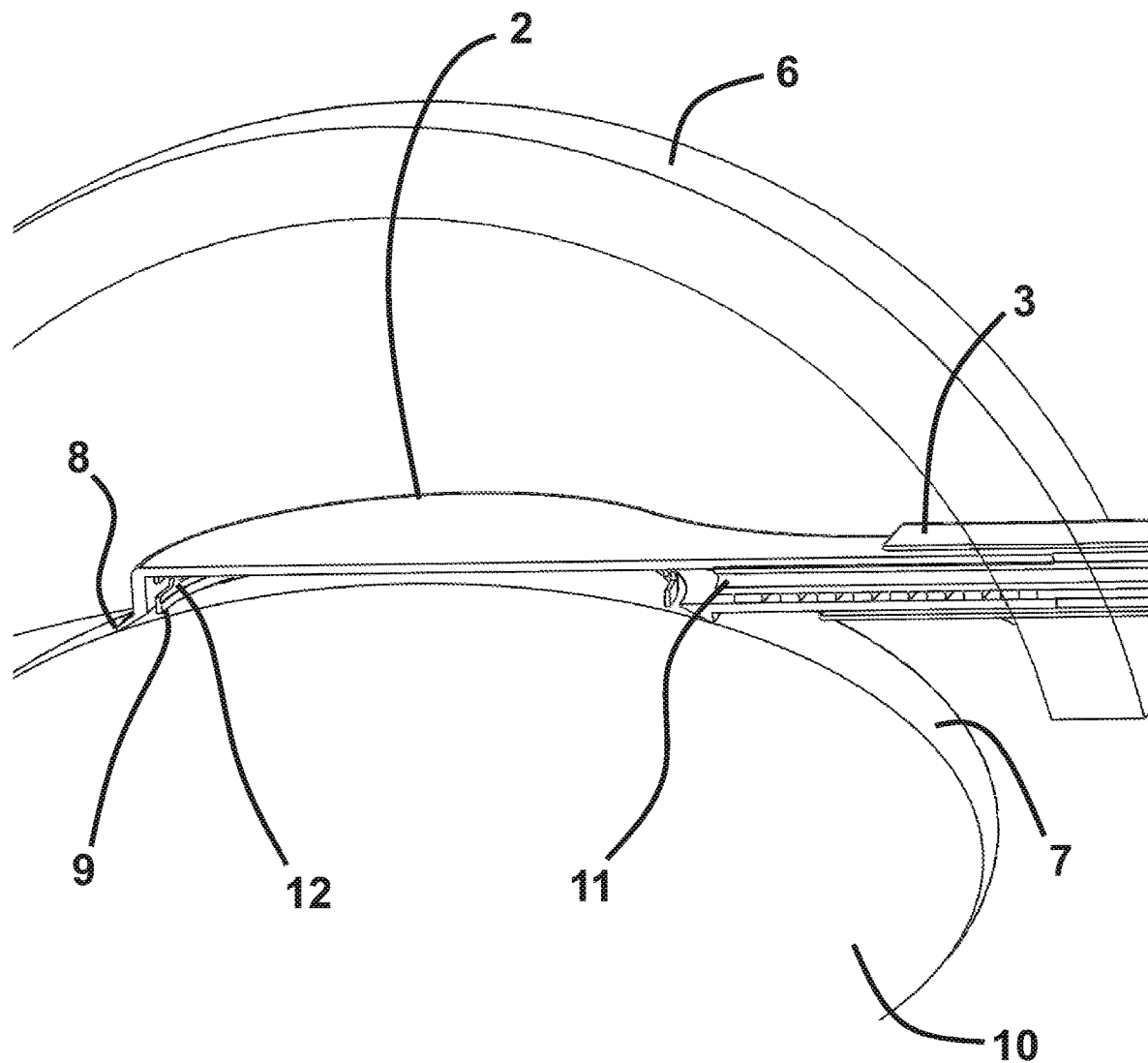
FIG. 2 is an expanded cross-sectional view of the microsurgery/capsulotomy device with a suction cup deployed and in contact with the lens capsule of the eye, according to an embodiment of the invention.

FIG. 2 shows a cross section of the device in use. The electrode 9 (e.g., cutting element) is in contact with the capsule 7, which encloses the lens 10. The electrode 9 is supported by an elastically deformable ring 12 (e.g., support structure). The suction cup 2 (e.g., elastomeric structure) has a "skirt" or "lip" 8 to facilitate the formation of a fluidic seal with the capsule when suction begins. Fluid flow through tube 11 controls the suction force.

Figure 3A:
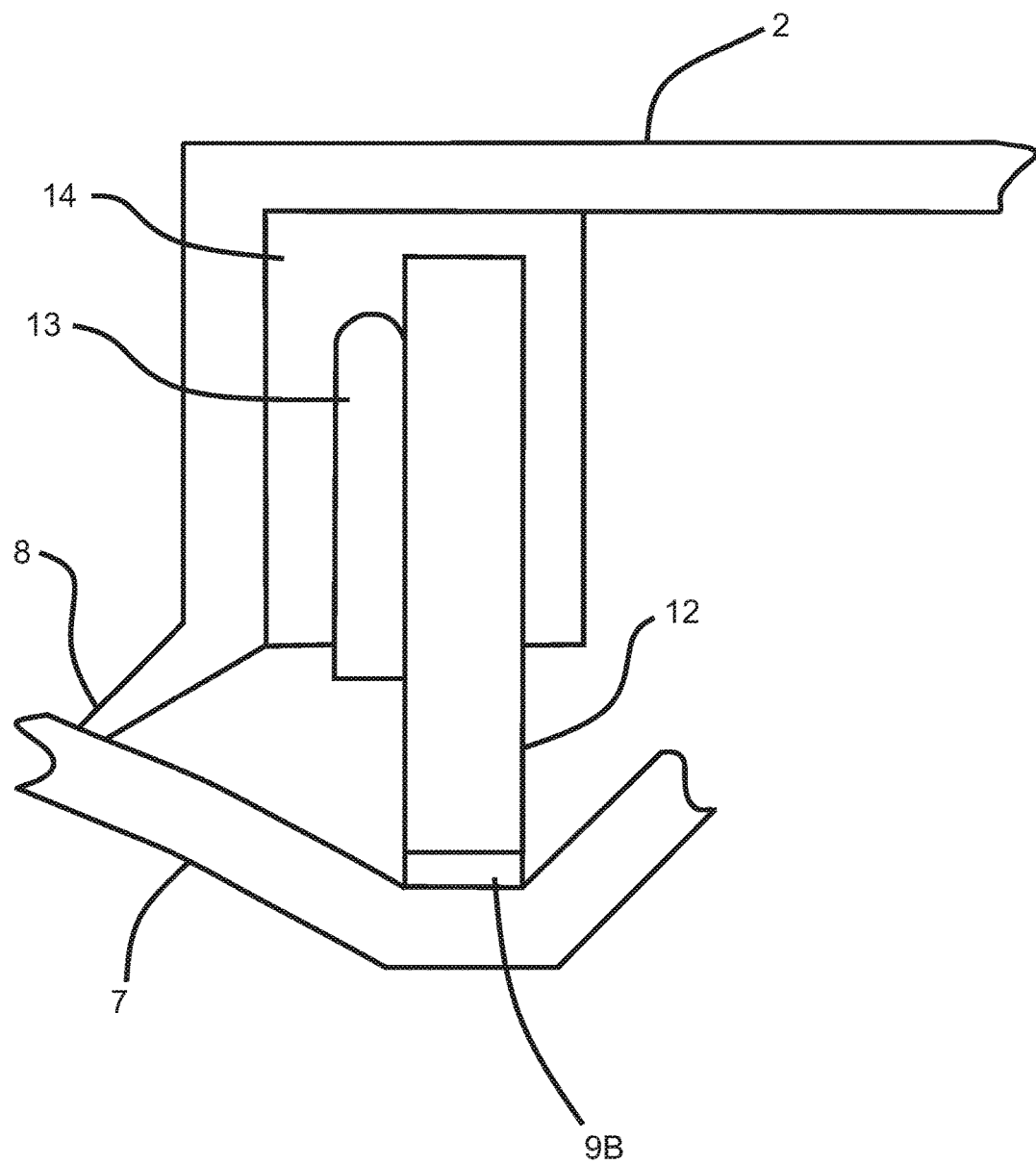
FIG. 3A is a schematic cross-sectional view of the capsular membrane in contact with the electrode and skirt of the microsurgery/capsulotomy device, according to an embodiment of the invention.

FIG. 3A shows a schematic cross section of the capsular membrane 7 forced by suction into contact with the electrode 9 (e.g., 9B, 9-OD (FIG. 3B), or 9-ID (FIG. 3B), and any combination thereof) and the skirt 8 of the suction cup 2. The electrode is mechanically supported by the elastically deformable ring 12, which is held to the suction cup by potting material 14. Electrical lead 13 brings electrical current to the electrode. In some embodiments, the electrode 9 is placed along the bottom of the support structure 9B, the inner diameter of the support structure 9-ID (FIG. 3B), along the outer diameter of the support structure 9-OD (FIG. 3B), or any combinations thereof. Some embodiments of this configuration are shown in more detail in FIG. 3C, as described below.

Figure 3B:
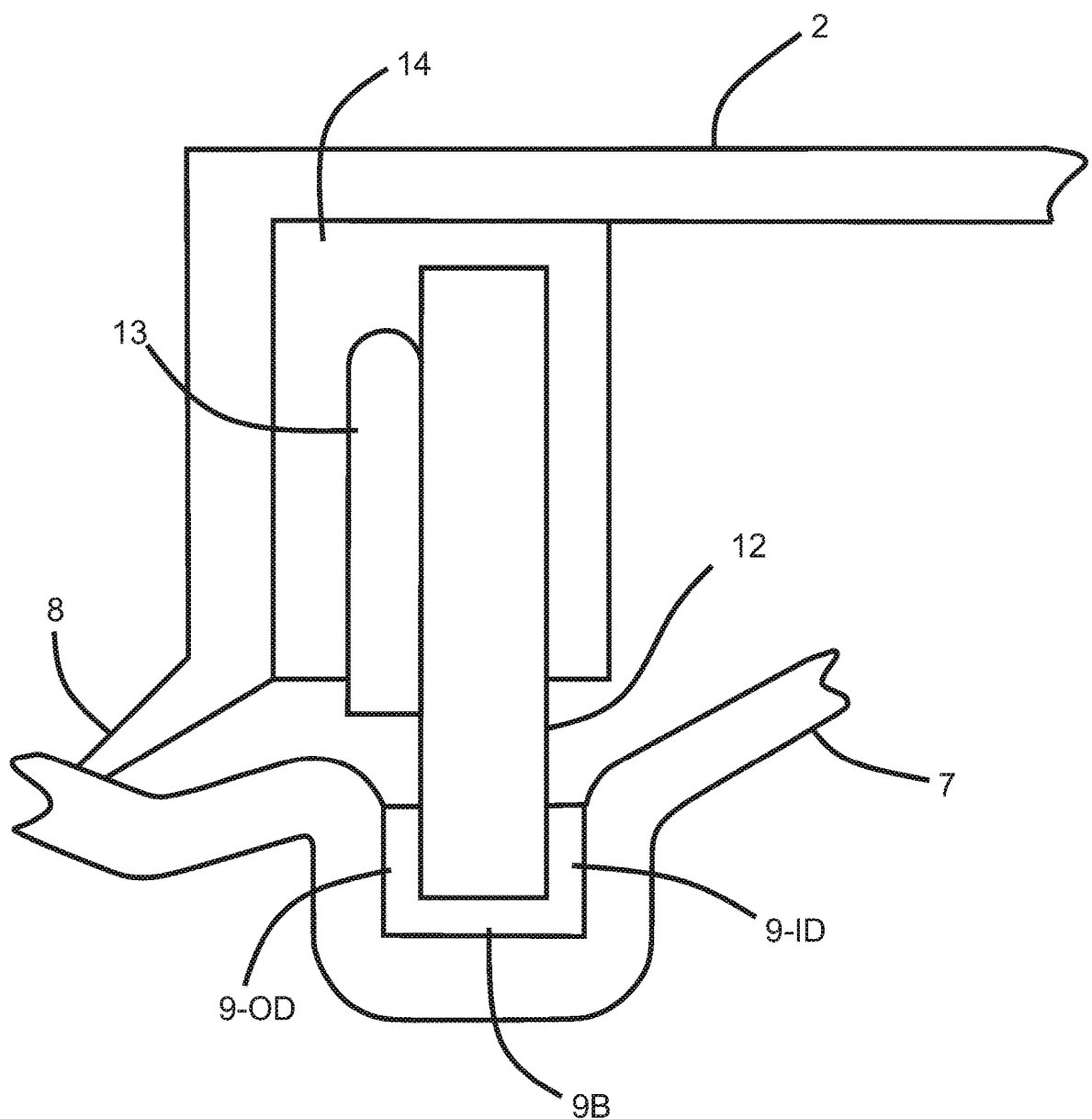
FIG. 3B is a schematic cross-sectional view of the capsular membrane in contact with the electrode and skirt of the microsurgery/capsulotomy device where suction has been applied between the capsular membrane and the suction cup, according to an embodiment of the invention.

FIG. 3B shows a modification of FIG. 3A where the suction has been increased to pull the capsule 7 into contact with the electrode 9 (e.g., 9B, 9-OD, or 9-ID, and any combination thereof) and the skirt 8 of the suction cup 2. The electrode is mechanically supported by the elastically deformable ring 12, which is held to the suction cup by potting material 14. Electrical lead 13 brings electrical current to the electrode.

Figure 3C:
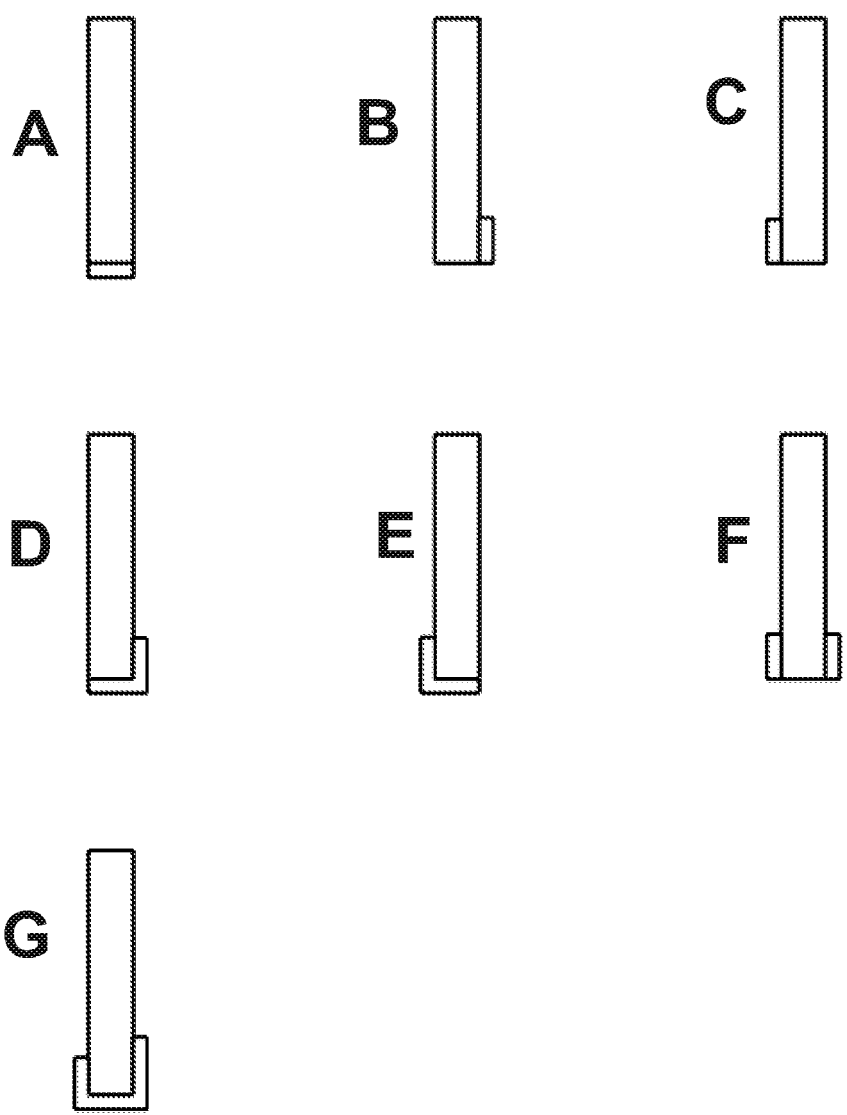
FIG. 3C shows cross-sectional views of electrode positioning along the electrode support ring according to certain embodiments of the invention.

FIG. 3C shows cross sectional views of seven locations where electrodes (e.g., gold) are plated on the bottom of the elastic support ring in certain embodiments of the invention. In some embodiments, the elastic support ring is made from superelastic nitinol. Each design results in a different magnitude and distribution of tensile and shear stresses in the membrane when suction is applied, and a different distribution of heat flow and resulting temperatures after the electrical discharge occurs. In one embodiment, the electrodes are configured differently for people whose capsules tear cleanly in shear (e.g., older adults) vs. designing electrodes for people whose capsules need high tensile stress to tear (e.g., younger adults and children), as discussed later in this application. FIG. 3C-A shows the electrode along the bottom of the support ring, according to an embodiment of the invention. FIG. 3C-B shows the electrode on the inner dimension of the bottom of the support ring, according to an embodiment of the invention. FIG. 3C-C shows the electrode on the outer dimension of the bottom of the support ring, according to an embodiment of the invention. FIG. 3C-D shows the electrode on the bottom and the inner dimension of the bottom of the support ring, according to an embodiment of the invention. FIG. 3C-E shows the electrode on the bottom and the outer dimension of the bottom of the support ring, according to an embodiment of the invention. FIG. 3C-F shows the electrode on the inner dimension and the outer dimension of the bottom of the support ring, according to an embodiment of the invention. FIG. 3C-G shows the electrode along the bottom, the inner dimension, and the outer dimension of the bottom of the support ring, according to an embodiment of the invention. These are just some examples of electrode designs, but the electrode can be otherwise positioned as desired. Different surface textures will trap different amounts of liquid (e.g., a viscoelastic or suitable lubricant) between the membrane and the electrode. A smooth surface along the electrode will maximize heat conduction from the electrode directly to the membrane. The various electrode designs illustrated in FIG. 3C can be used with any of the devices described in this application.

Figure 4:
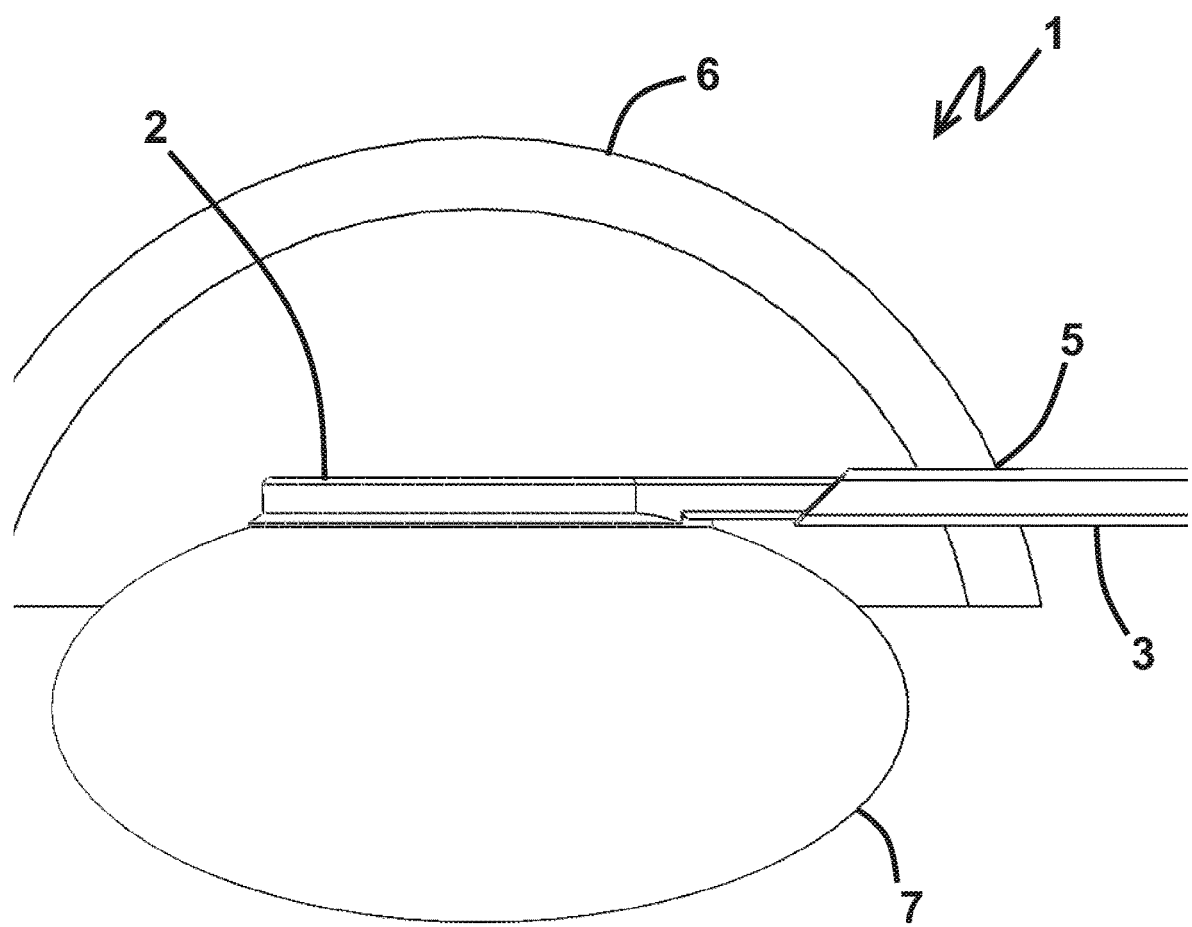
FIG. 4 is a side perspective view of the microsurgery/capsulotomy device with the suction cup deployed and in contact with the lens capsule of the eye, according to an embodiment of the invention.
Figure 5:
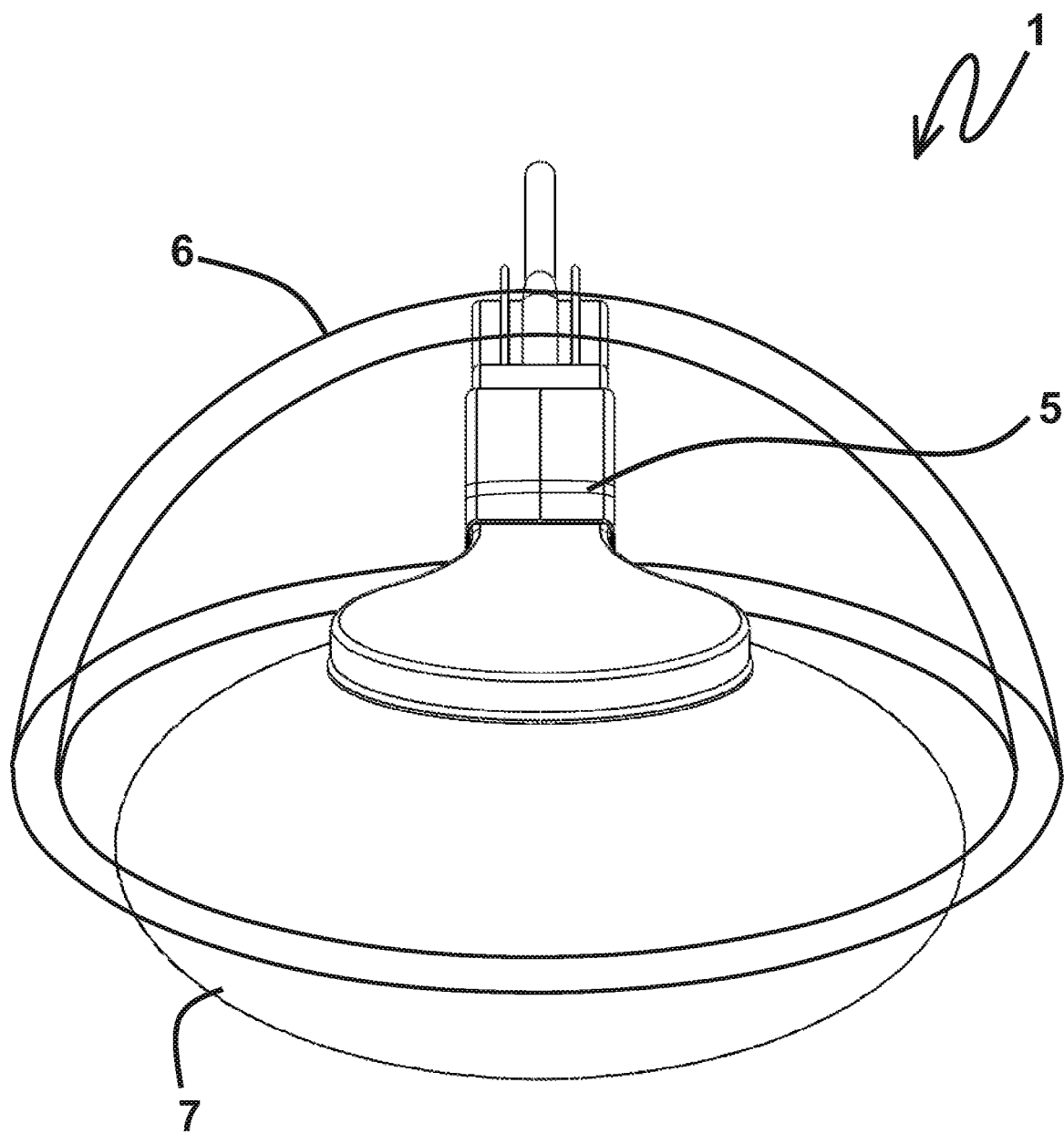
FIG. 5 is a front perspective view of the microsurgery/capsulotomy device with the suction cup deployed and in contact with the lens capsule of the eye, according to an embodiment of the invention.
Figure 6:
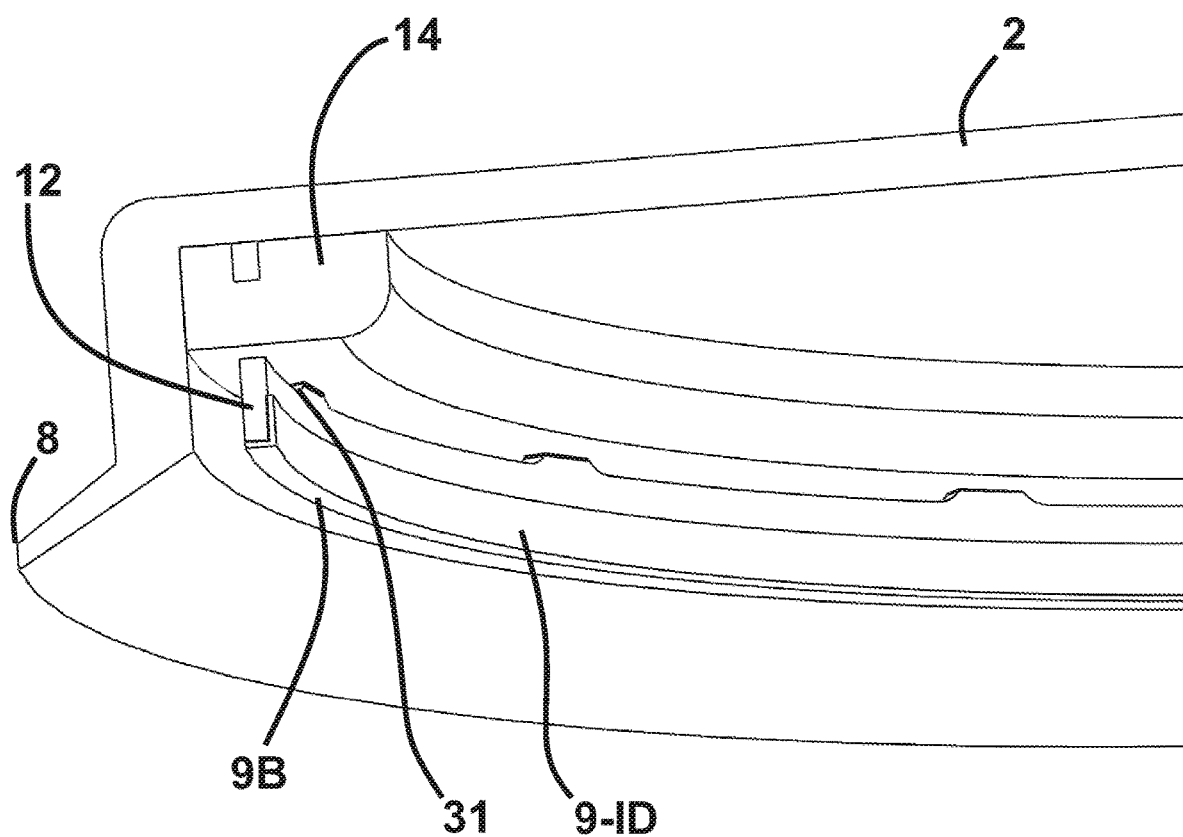
FIG. 6 is a cross-sectional view of the device showing the relationship between the elastomeric suction cup, electrode support ring, electrode, potting material, and suction cup skirt, according to an embodiment of the invention.
Figure 7:
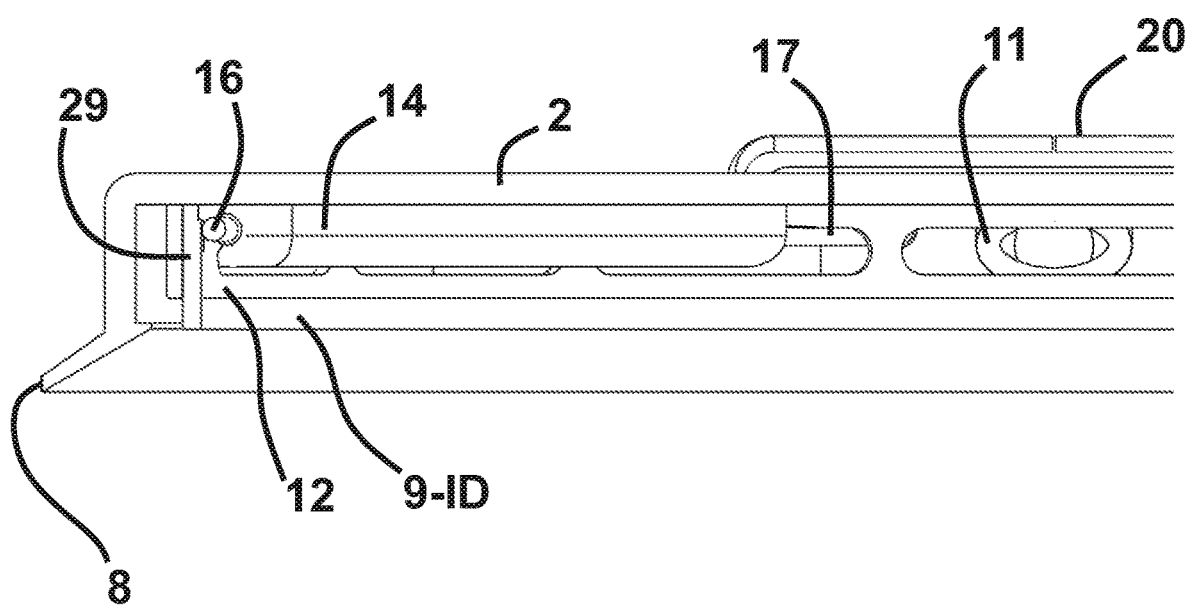
FIG. 7 is a partial cross-sectional view of the microsurgery/capsulotomy device showing the positioning of the suction tube, the leading edge of the inserter, the electrical lead wire, the end of the wire, and the electrode bond pad, according to an embodiment of the invention.

FIG. 4 shows a side view of the device 1 in use in the cornea and resting on the capsular membrane of the lens. FIG. 5 shows a front view of the device 1. FIG. 6 shows a sectional view of the device with the elastomeric suction cup 2, electrode ring support 12, electrode 9 (9B, 9-ID), potting material 14, and suction cup skirt 8. In one embodiment, the electrode ring support 12 is nonconductive or less conductive than the electrode 9 to prevent heating of the suction cup 2. In another embodiment, slots or one or more other discontinuities are introduced into the top of the electrode support ring 12 to prevent current flow around the top of the electrode support ring, and thus prevent heating of the suction cup 2. In one embodiment, the electrode support ring comprising slots is of the same material as the electrode. In another embodiment, the electrode and electrode support ring are part of a continuous structure, with the electrode defined as the part that allows current flow and contacts the capsular membrane of the lens or other tissue to induce a tear along the electrode. The portion of the structure serving as the electrode support ring does not allow current flow and is in contact with the elastomeric structure. This embodiment also avoids heating of the suction cup. FIG. 7 shows a front cross-sectional view of the device showing the suction tube 11, the leading edge 20 of the inserter 3, the insulated electrical lead wire 17, and the end 16 of the wire 17 that is bonded to an electrode bond pad 26 (see FIG. 8).

Figure 8:
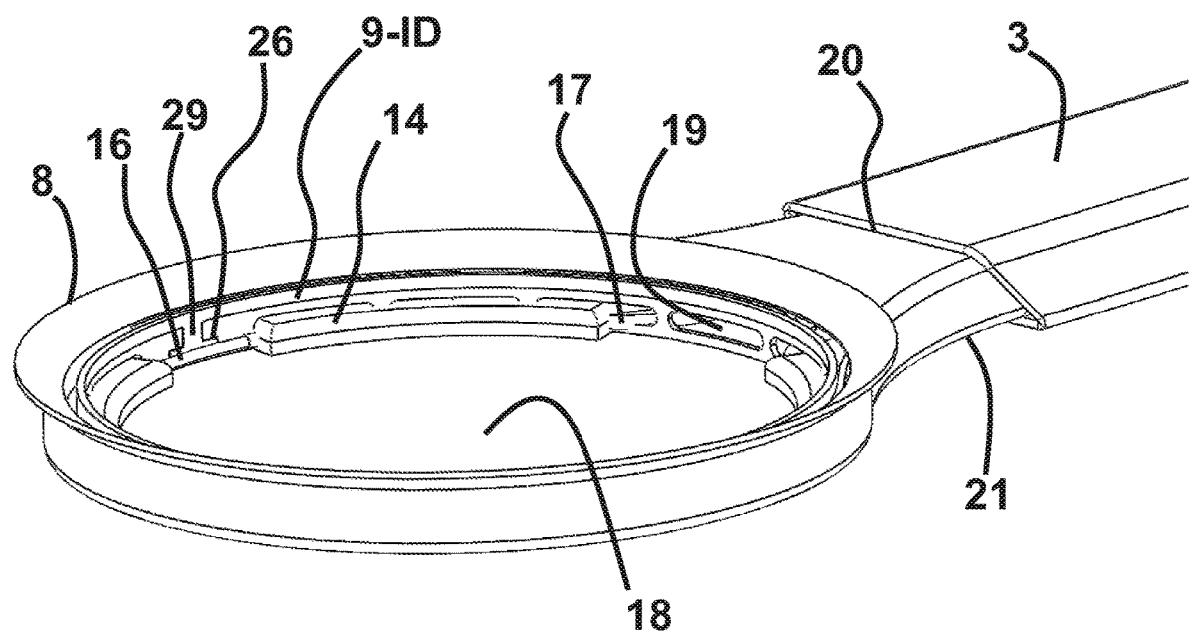
FIG. 8 shows a bottom view of the microsurgery/capsulotomy device, according to an embodiment of the invention.

FIG. 8 shows a bottom view in which can be seen an electrode bond pad 26, and a connecting trace 29 from the bond pad to the electrode. The support ring 12 has openings or holes 19 which allow the potting material 14 to lock the ring into place, or where there is no potting material, to let fluid flow occur to establish suction. The holes 19 also help to avoid kinking in the electrode when expanding from a compressed state. The suction cup has an elastomeric neck region 21 that connects to the stem. During use, the suction force will deform the suction cup and pull the surface 18 into contact with the lens capsule. In some embodiments of the present invention, means are provided to make the capsule stick to surface 18 sufficiently well that the excised circular patch of membrane is carried out of the eye with the device when it is withdrawn. This sticking force may be provided, in some embodiments, by chemical groups that stick to collagen of the membrane, or by micromechanical sharp points, or by a combination of sharp points coated with sticky chemicals. In one embodiment, a small point of sticky material (e.g., partially cured silicone gel) is applied to center of roof. In another embodiment, a small patch of roof 18 is coated with sticky material (e.g., silicone gel). This sticky patch is coated with a soluble non-sticky layer (e.g., polyvinyl alcohol, PVA) to prevent self-adhesion during compression of the patch to enter the eye. After less than about one minute in the eye the PVA will diffuse away, and the viscoelastic solution will flow out of the interface sufficiently (due to suction pressure) for the sticky coating to contact the membrane. In certain embodiments, the texture of the roof 18 will have hills and valleys molded into it to allow fluid to flow out of the interface and not get trapped. This allows the surface 18 to contact the membrane enough to stick to it and remove the excised patch out of the eye.

Another mechanism to contribute towards the retention and removal of the excised patch is a localized vacuum line that touches the patch. This can be a separate line from the main suction line so that it can still apply a vacuum to the patch during the step when the main suction line is supplying material back to the suction cup to break its grip on the lens. Another mechanism to contribute towards the retention and removal of the excised patch is micromechanical sharp points located along and within the suction line.

Figure 9:
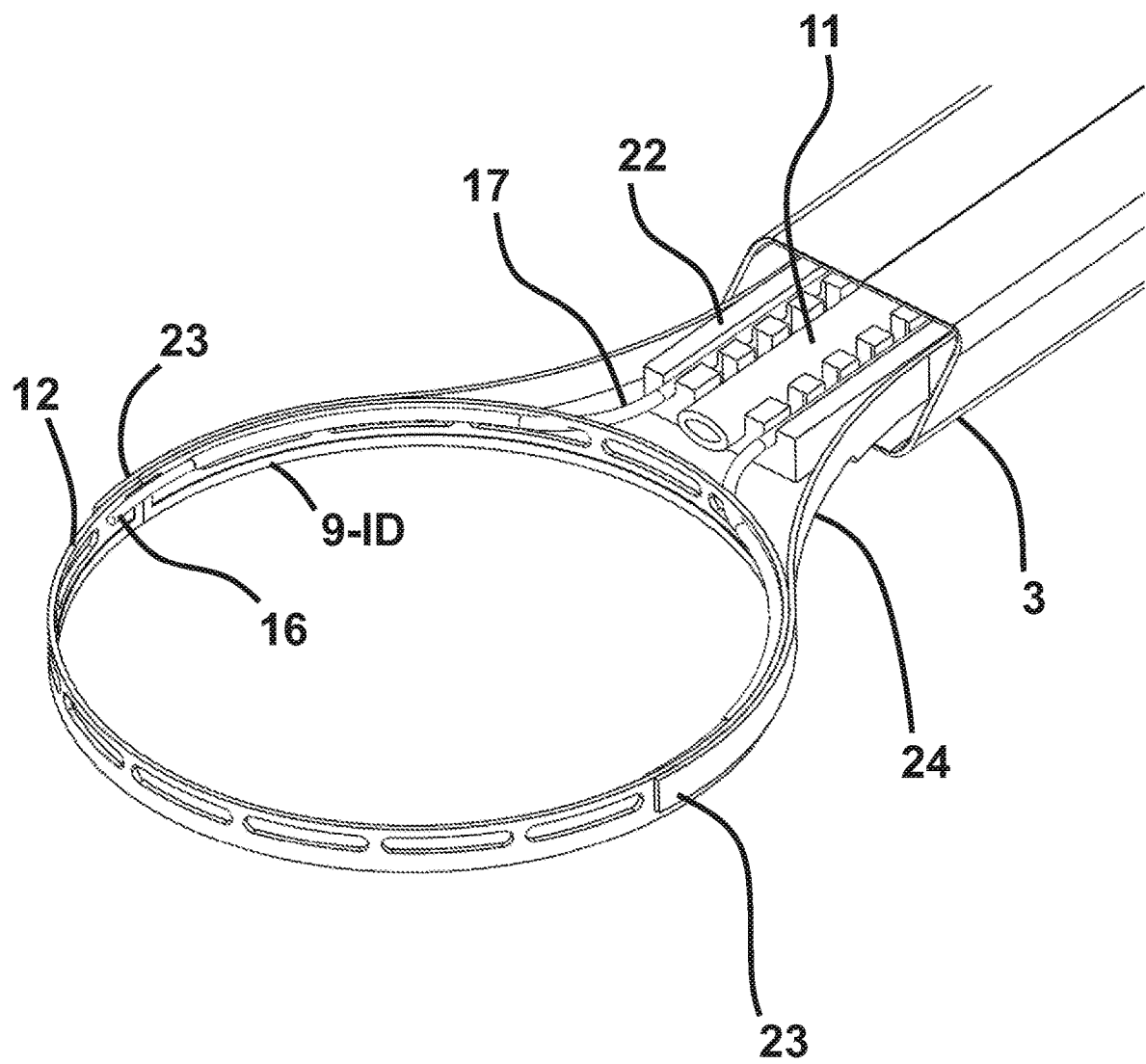
FIG. 9 shows a top view of the microsurgery/capsulotomy device, showing the resistive heating device without an elastomeric suction cup, according to an embodiment of the invention.

FIG. 9 shows the device as it would appear without the suction cup or potting material in the way. An elastically deformable support arm 24 is bonded (e.g., by spot welding) to the elastically deformable ring 12 over the region 23. In one embodiment, the elastically deformable ring 12 and the support arms 24 are made from superelastic nitinol and the support arms 24 are bonded to the elastically deformable ring 12 by welding (laser welding, or electrical resistance spot welding). The nitinol members may be cut (e.g., by laser) from strips of foil, and may undergo the shape setting process prior to welding. The support arms are attached to stem block 22, which also anchors the insulated wires 17 and the suction tube 11 within the lumen of the stem (not shown). The stem block 22 has a structure that mechanically locks it to glue or potting material (e.g., silicone or polyurethane) that bonds to the neck 21 of the suction cup (silicone cup to stick to silicone potting, or polyurethane cup to stick to polyurethane potting).

Figure 10:
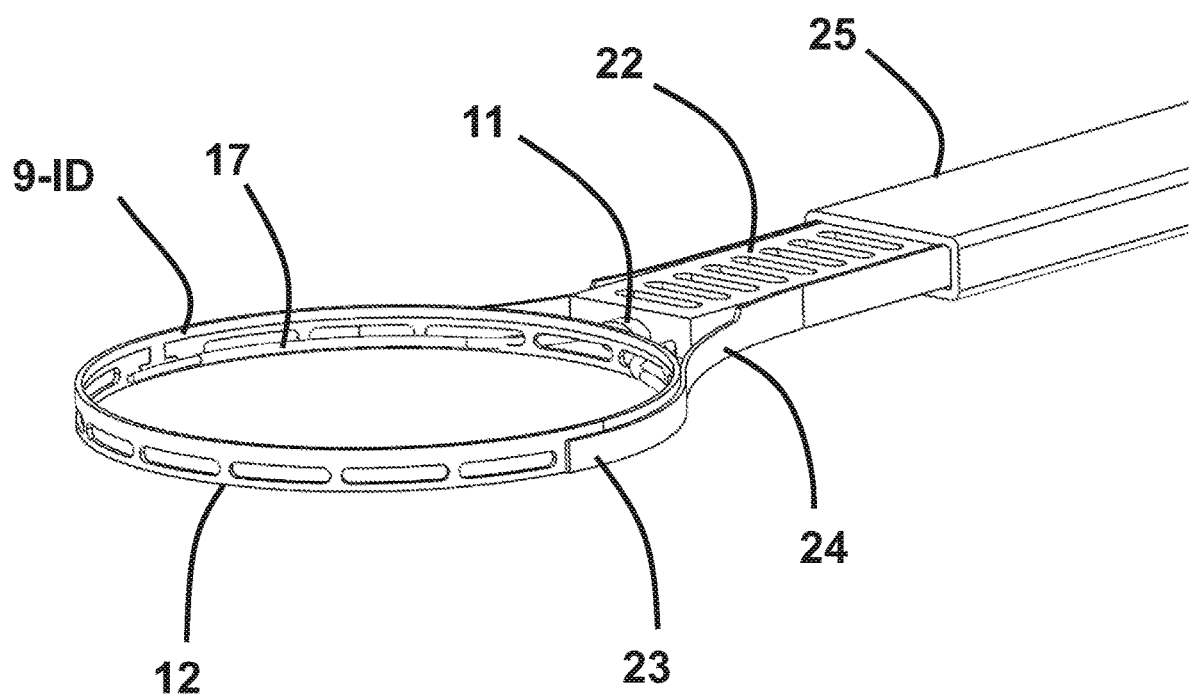
FIG. 10 shows a top view of the microsurgery/capsulotomy device showing the outer layer of the stem structure and the components located within the stem structure, according to an embodiment of the invention.

FIG. 10 is similar to FIG. 9, but the inserter has been removed and the outer layer 25 of the stem structure can be seen. In one embodiment this outer layer is comprised of heat shrink tubing (e.g., polyester less than about 0.1 mm in thickness).

Figure 11:
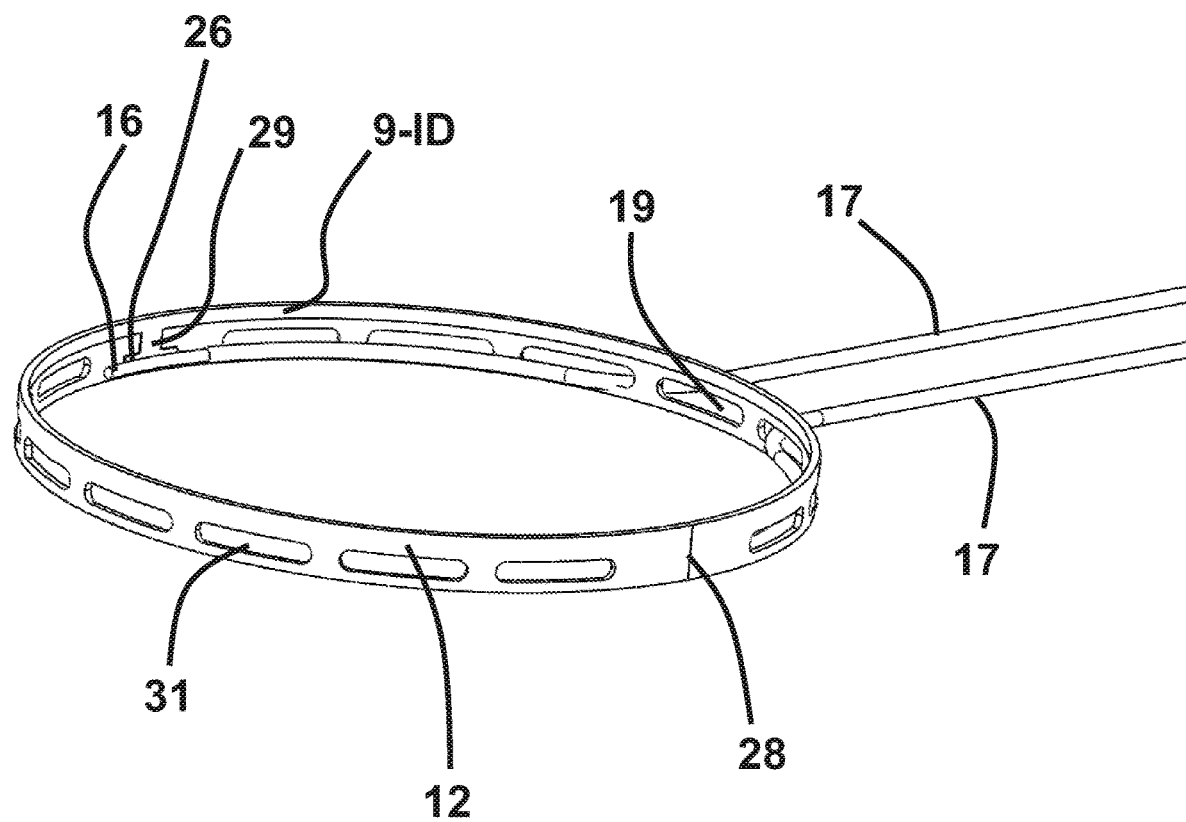
FIG. 11 shows the interface between the wires providing current to the electrode located on the electrode support ring, according to an embodiment of the invention.

In FIG. 11 (oriented with the bottom surface facing up) can be seen the electrode 9 (9-ID), electrical connecting path 29, bond pad 26, bonded wire end 16, the optional weld 28 (may be present if the ring is made from an initially flat foil), thru hole 19 allowing fluid flow for suction, and thru holes 31 to provide locking engagement with potting material. The dimensions of the thru holes 31 and 19 allow for fine-tuning of the stiffness of the elastic ring for a given available thickness of foil or sheet stock. The stiffness must be high enough to ensure that the ring can return to its circular shape inside the anterior chamber, but it should be as low as possible to minimize friction forces for sliding inside the inserter 3.

In some embodiments of the invention, the electric current flows in one lead, and to the electrode via connecting path 29. Then, half the current flows clockwise through one half of the circular electrode, and the other half of the current flows counterclockwise though the other half of the circular electrode, to the other lead (180 degrees from the first lead) via another connecting path (not shown) to ground. In one embodiment, the source of the electrical current is a capacitor that has been charged to a predetermined voltage.

In this section, we describe an embodiment of the device to thermally isolate the heated electrode from the elastomeric suction cup to avoid the possibility of outgassing. The electrode may reach a temperature of 1000° C. (or within the range of 500° C. to 1300° C.) for 0.0001 second (or within the range of 0.00001 sec to 0.001 sec). In one embodiment of the present invention, a good electrical conductor, such as gold, is used to form the electrode. Other materials such as copper, silver, graphite, graphene, carbon nanotubes, etc., may also be used as an electrical conductor. In one embodiment, the supporting ring is superelastic nitinol. If the gold is plated directly on bare nitinol metal, good adhesion can be achieved so it will not come off in use. Part of the electrical current will go through the gold, and part will go through the nitinol. The fraction of current that goes through each path depends on the resistance of the path. Gold is about 34 times more conductive than nitinol in the austenitic phase (and about 33 times more conductive than the martensitic phase). The superelastic nitinol free of applied stress is austenitic above about 8° C., and only forms the martinsite phase where stress exceeds a certain threshold during the deformation to get through the corneal incision. Since the power dissipated through a resistor is $P=I^2R$, in one embodiment, we maximize the current in the smallest possible volume to maximize the power density so the power density will be high in the gold and low in the nitinol. Also the specific heat of gold is about ⅓ that of nitinol. For the same energy dissipated in the same mass of material the temperature rise in the nitinol will only be ⅓ as much as the gold. Thus, in one embodiment, the mechanical connection to the elastomer is made through nitinol. In this embodiment, the maximum temperature that reaches the elastomer will be kept below a value at which outgassing would become a concern.

In one embodiment of the invention, the dimensions of the elastic ring 12 and electrode are as follows: Nitinol ring—Outer diameter: 5.5 mm, inner diameter: 5.45 mm, height 0.4 mm. Plated gold—thickness: about 0.01 mm or less, width: 0.1 mm, areas to plate: (1) Inner diameter edge, (2) outer diameter edge (3) bottom edge, (4) any combination of these (see, e.g., FIG. 3B, and FIG. 3C Embodiments A-G).

In some embodiments, the nitinol is covered by an electrically insulating layer prior to gold plating. In one embodiment, a method to cover nitinol with an electrically insulating layer prior to gold plating is as follows:

1. Laser cut nitinol parts from foil.
2. Electropolish the nitinol parts.
3. "Set-shape" the nitinol ring and support arms (in their respective fixtures at about 500° C. for about 10 minutes, then quench the components in water).
4. Weld (e.g., laser, tig, or resistance welding) ring edges 28 together (optional).
5. Optionally weld nitinol support arms to ring.
6. Grow thermal oxide in controlled atmosphere furnace.
7. Set nitinol structure in shadow mask.
8. Sputter adhesion layer (e.g., 250 Angstroms to 1000 Angstroms Ti).
9. Sputter seed layer (e.g., 250 Angstroms to 1000 Angstroms Au (or Ni)).
10. Remove from shadow mask.
11. Plate gold (for example 10 microns thick).

The device generated by the method above will inhibit flow of current through the nitinol during use of the device (because of the insulating layer). This will decrease the temperature rise seen by the elastomeric structure, and the device will be more efficient. Although gold may still be used as a conductor, other conductors having lower conductivity may be used as the functioning of the device no longer depends on the ratio of conductivities of the electrode material to the nitinol ring. Thus, in some embodiments, a higher melting point material such as nickel, stainless steel, or superelastic nitinol, may be used as material for the heated electrode. These materials have higher resistivity, so a higher voltage discharge will be needed to get the same power in the same short duration pulse as achieved in gold. In a preferred embodiment, the insulating layer (e.g., oxide or nitride) will be thick enough to prevent significant electron transport from the electrode to the elastic support ring during the discharge for the chosen applied voltage.

Many techniques are known in the art to accomplish the goal of attaching a gold electrode to a supporting superelastic nitinol ring. With the nitinol as a flat sheet, photolithography may be performed to mask where plating is not desired. In another technique, after shape setting and welding, photolithography may be performed on the cylindrical surface prior to gold plating.

Figure 12:
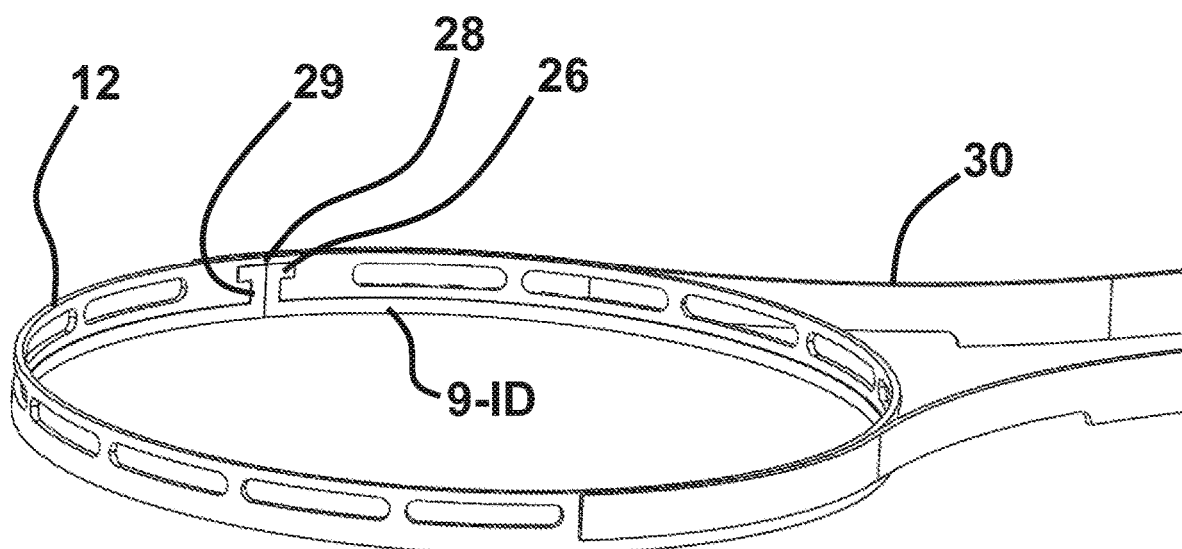
FIG. 12 shows an embodiment of the device in which the support arms are plated with an electrically conductive substance and attached to the electrode support ring and electrode.
Figure 13:
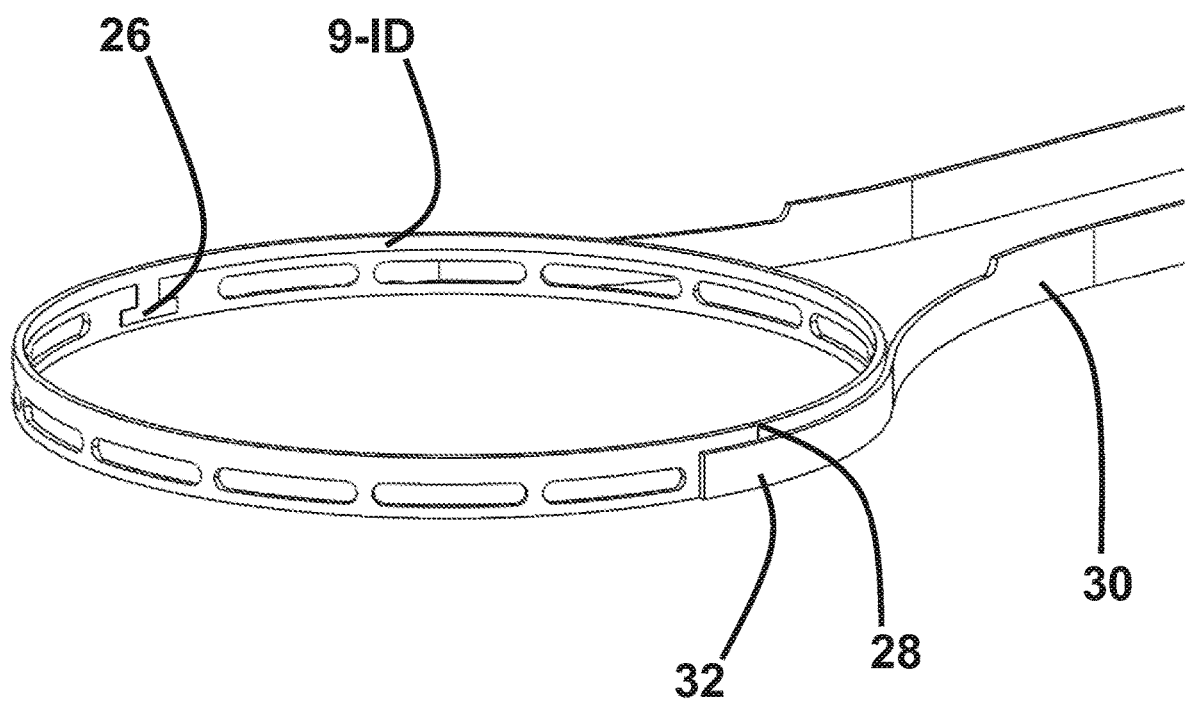
FIG. 13 shows another view of an embodiment of the device in which the support arms are plated with an electrically conductive substance and attached to the electrode support ring and electrode.

FIGS. 12 and 13 show an embodiment of the device in which the nitinol support arms 30 have been plated with gold to serve as the electrical leads to the electrode. This allows the removal of the wires 17 from the suction cup and stem. In one embodiment, the cross-sectional area of the gold on the support arms is much greater than that of the electrode, so the support arms do not get hot in use. Thru holes in the nitinol ring allow thru plating of the gold such that gold to gold bonding (or soldering) can be used to make the mechanical connection of the support arm to the electrode support ring, and the electrical connection of the electrically conductive support arm to the electrode. Any of the devices described herein could be modified to include this design including conductive support arms. In one embodiment, the support arm is modified to comprise a channel or tube for applying suction (e.g., the support arms are provided in the shape of u-shaped channels to form a tube for applying suction (see, e.g., FIG. 25)).

Figure 14:
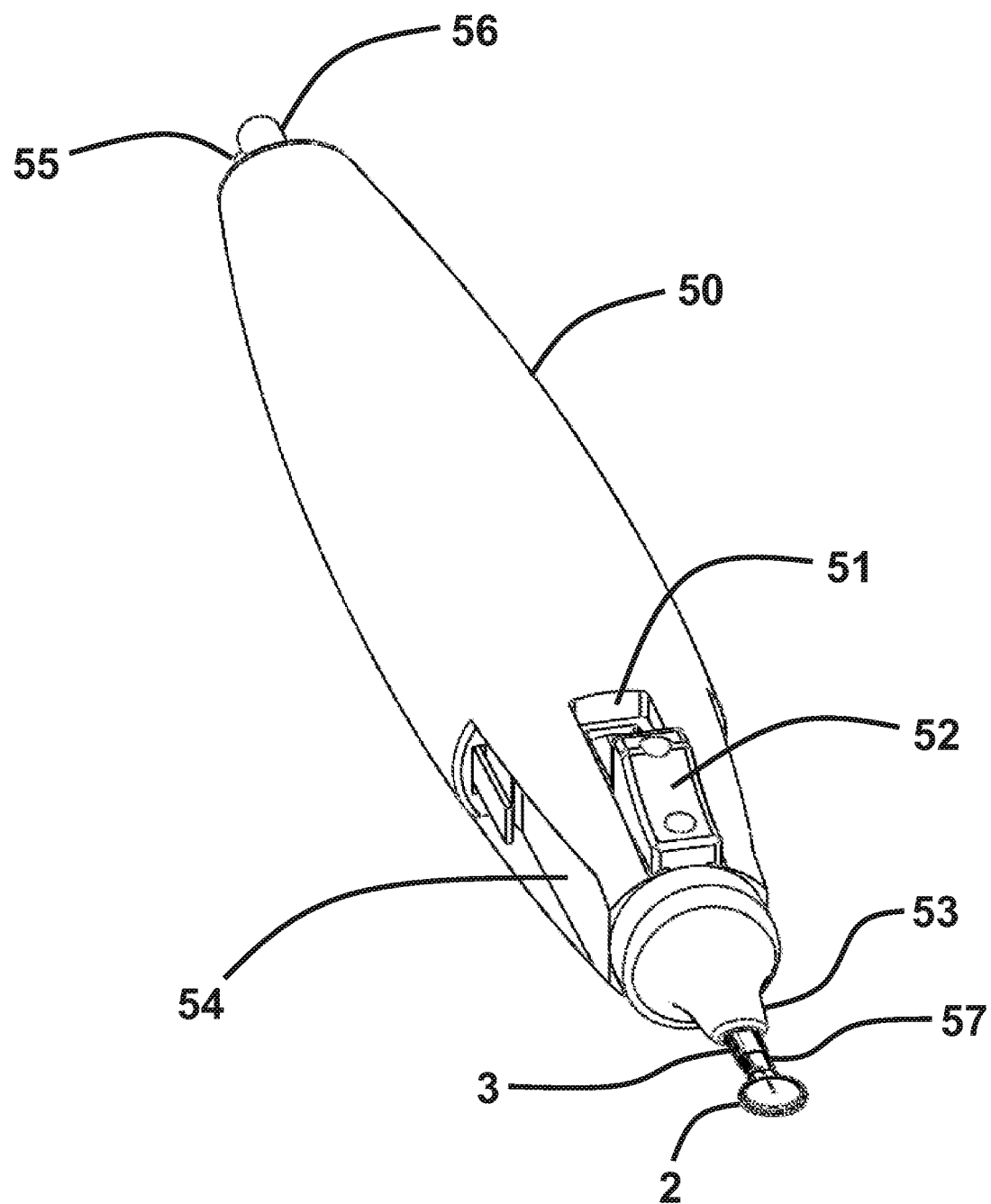
FIG. 14 is a top perspective view of the microsurgery/capsulotomy device with the suction cup deployed, according to an embodiment of the invention.

FIG. 14 shows an overview of the device mounted on a handpiece, according to an embodiment of the invention. There are two assemblies: the outer housing, and the inner unit that slides relative to the outer housing. The outer housing is comprised of sleeve 50, nosepiece 53, and inserter 3. The inner unit is comprised of tubing to conduct suction 56, electrical conductors 55, thumb slide 52, and stem 57. To move the sliding unit, the surgeon pushes the thumb slide 52 along guide slot 51. A side channel 54 on each side of the sleeve 50 engages the latching arms 61 (see FIG. 17) of the compression chamber 60 (see FIGS. 17, 18).

Figure 15:
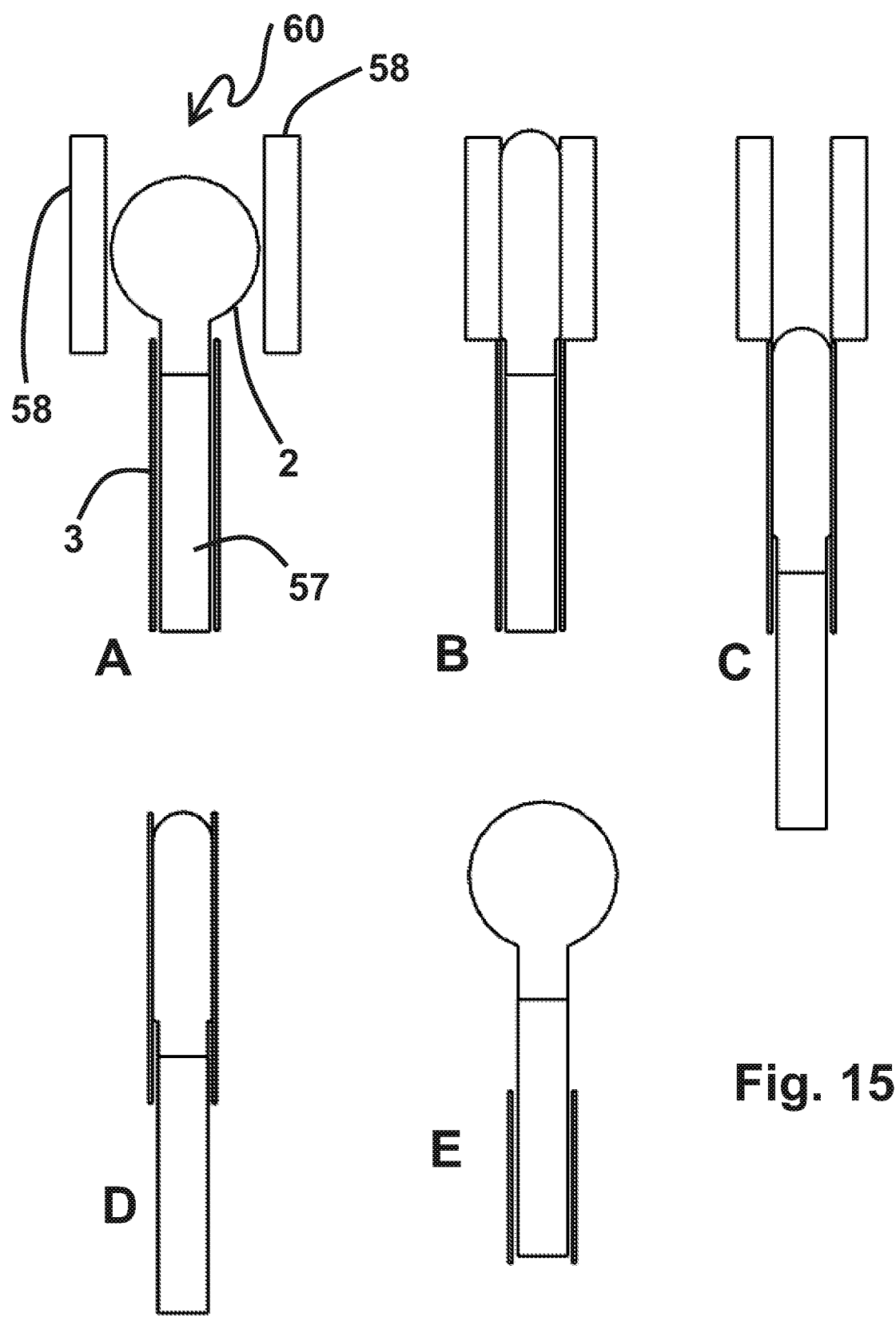
FIG. 15 shows the conceptual sequence of steps for compression of the suction cup to fit inside the inserter for entry into the eye, according to an embodiment of the invention.

FIG. 15 shows, according to an embodiment of the invention, a sequence of steps in deploying the device through a corneal incision:
1. As packaged, the suction cup 2 is located between compression beams 58 in the compression chamber 60 (Step A).
2. The user pushes the compression beams together so the suction cup is narrower than the inserter lumen width (Step B).
3. The suction cup is pulled into the inserter (Step C).
4. The compression chamber is unlatched from the handpiece and discarded (Step D).
5. The inserter is inserted into the corneal incision, and the suction cup is pushed out of the inserter (Step E).

Figure 16:
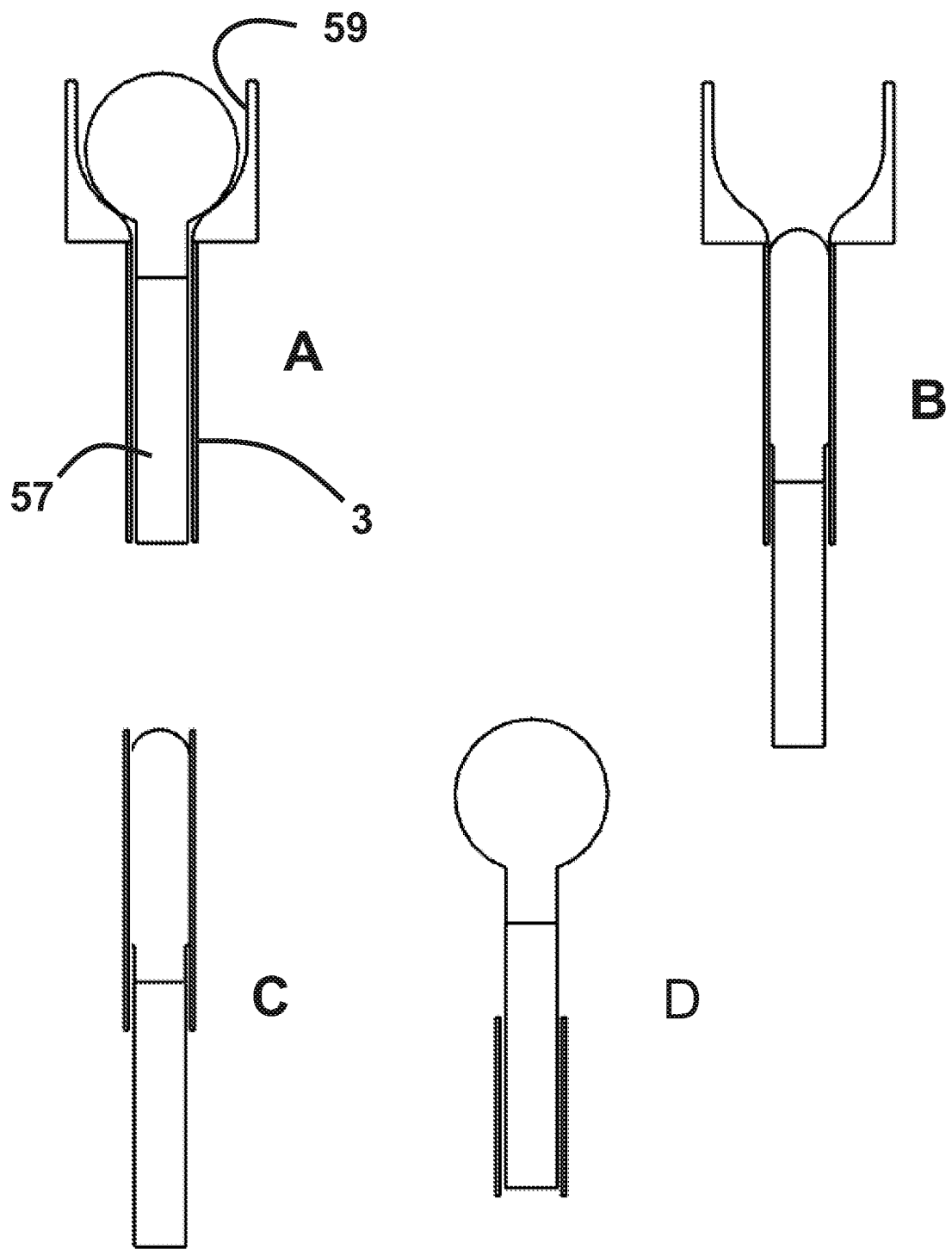
FIG. 16 is a top perspective view of a low friction compression device with converging sidewalls, according to an embodiment of the invention.

FIG. 16 shows the sequence of steps in deploying the device using a funnel-like passive compression structure 59. The suction cup undergoes compression as the user moves the thumb slide 52 away from the compression chamber. In this embodiment, converging sidewalls 59 gradually compress the suction cup 2 as it is pulled into the inserter 3. In one embodiment, friction is low because the compression chamber is flooded with saline, or viscoelastic, or other lubricants, prior to use. The floor and roof of the compression chamber physically constrain the suction cup or electrode, and prevent the suction cup or electrode from deflecting out of plane, shown in Step A. Without the shaped converging sidewalls, all of the work of compression would have to occur at the entrance to the inserter and the required force would be greater. In Step B, the suction cup is fully inside the inserter. In Step C, the compression chamber has been removed. Step D shows the device as it would appear after the inserter has been pushed through the corneal incision and the suction cup deployed within the anterior chamber. In one embodiment, the low friction compression device is used for a device comprising an electrode ring and electrodes alone without a suction cup.

Figure 17:
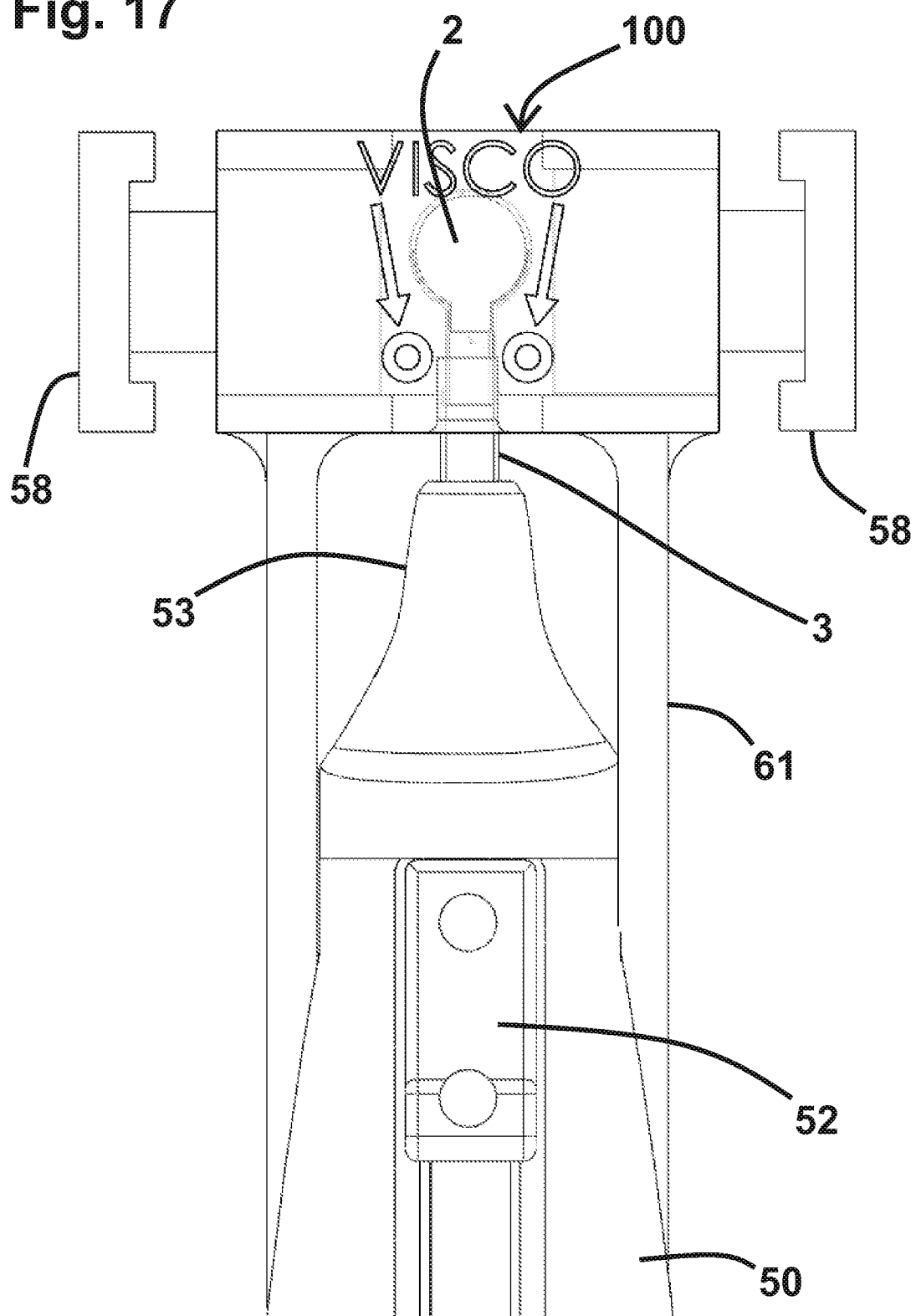
FIG. 17 shows the compression chamber with the suction cup stored inside a compression chamber, according to an embodiment of the invention.

FIG. 17 shows a plan view of a compression chamber 100 latched on to a handpiece sleeve 50 by means of latching arms 61, according to an embodiment of the invention. As packaged, the suction cup 2 is not under stress, and is located within the compression chamber, which will constrain it from vertical deflection when the compression beams 58 are moved toward each other to compress the suction cup.

Figure 18:
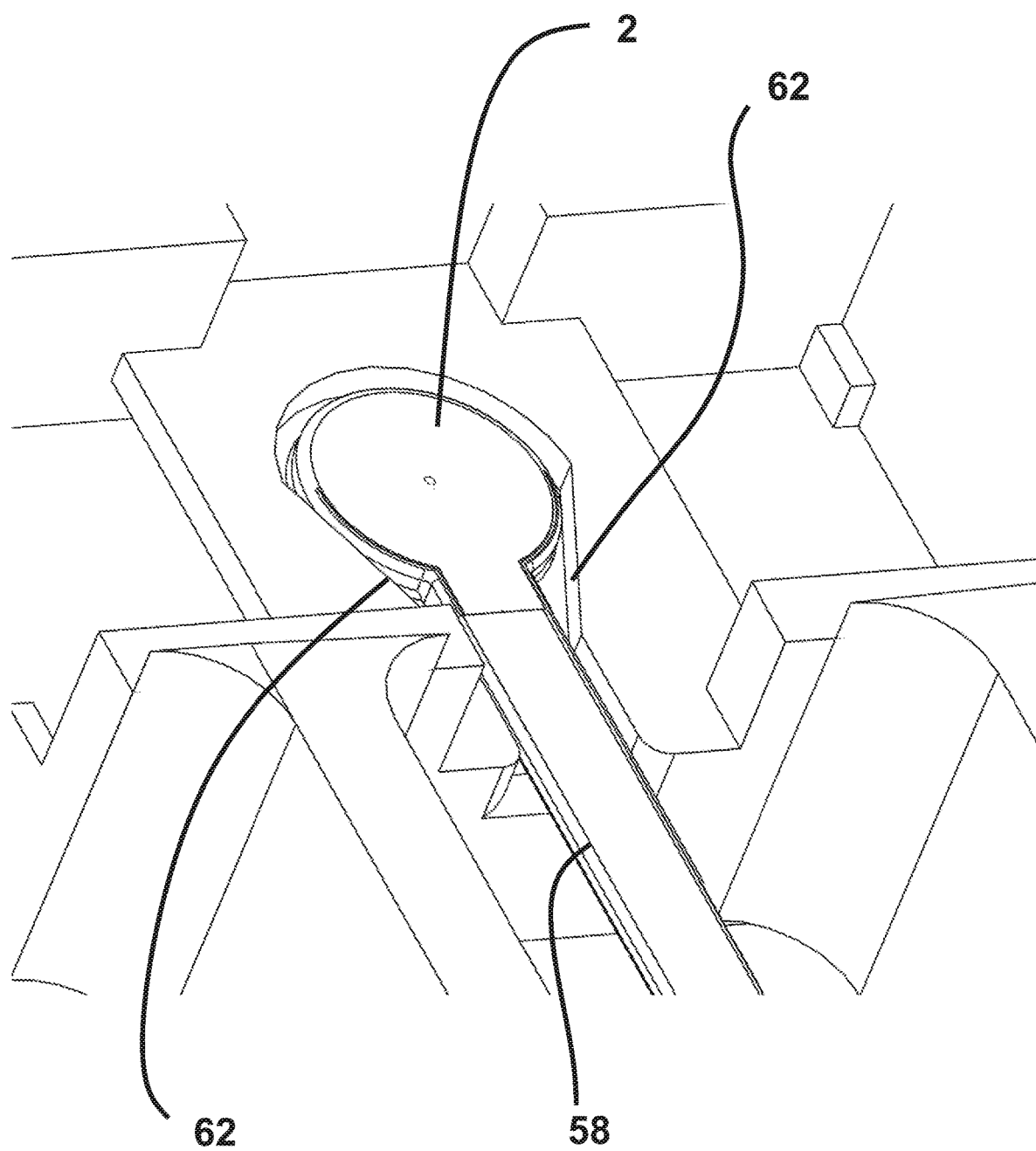
FIG. 18 shows an expanded view of the suction cup stored inside a compression chamber, according to an embodiment of the invention.

FIG. 18 shows a passive compression chamber having a 2-dimensional funnel-like shape with converging walls 62 which compress the suction cup 2 as it is slid out of the chamber and into the inserter, according to an embodiment of the invention. Any of the devices described herein could be used with the handpiece and methods of FIGS. 14-18.

Figure 19:
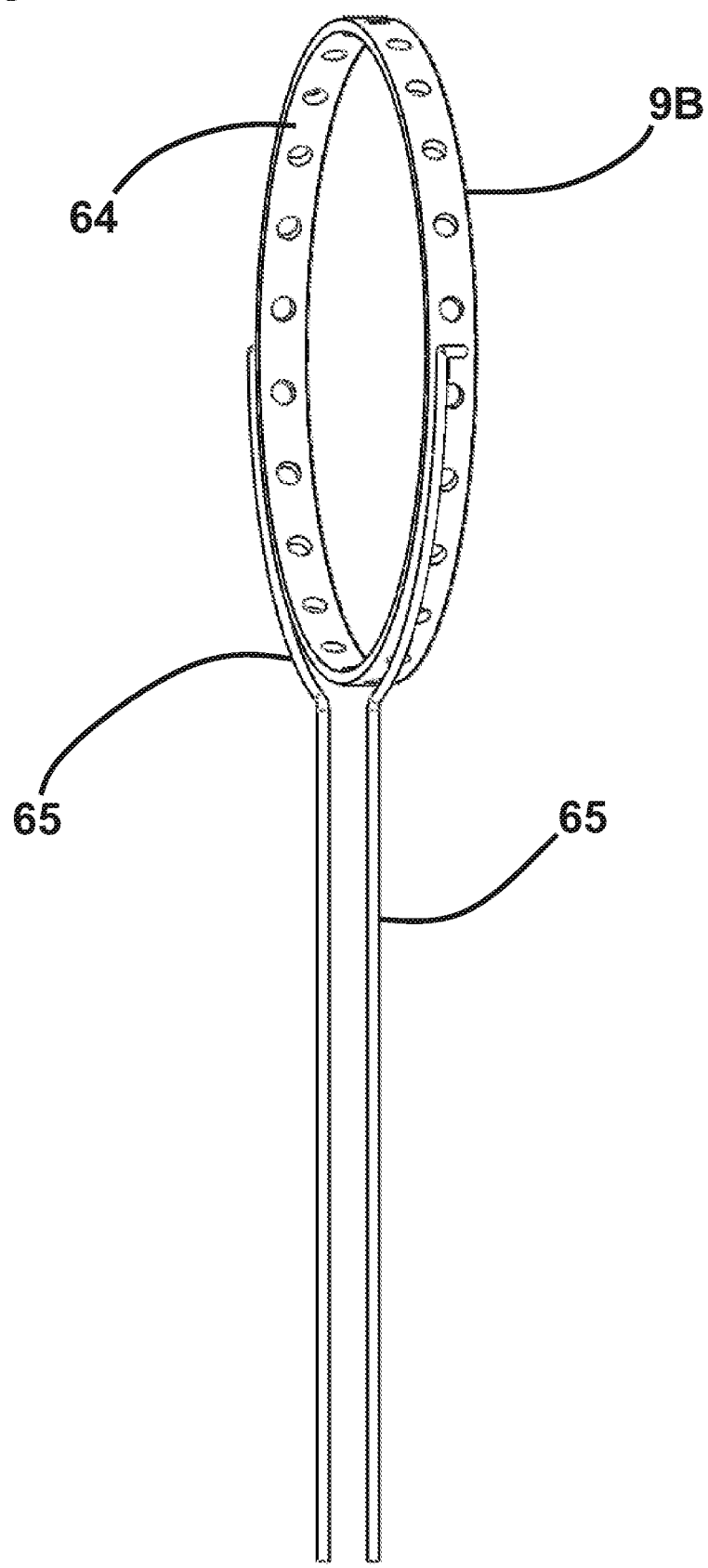
FIG. 19 shows an embodiment of an electrode support ring configured to be attached to wire leads to provide current to the electrode.

FIG. 19 shows an elastic ring 64 made of, e.g., nitinol, or stainless steel. In one embodiment, the elastic ring 64 is made of stainless steel and the elastic ring will be of sufficient dimensions (e.g., a wall thickness of about 0.01 mm, up to about 0.025 mm) to avoid permanent plastic deformation during the deflection needed to insert it into the eye. In another embodiment, the elastic ring 64 is made from superelastic nitinol. In this case, the ring may be thicker (e.g., a wall thickness of about 0.05 mm up to about 0.075 mm). FIG. 19 shows an embodiment comprising wire leads 65 attached to the ring. This embodiment allows electrodes to float with less stiffness since the support arms are wires, allowing the device to have increased pitch and roll range of movement. This embodiment may be used with or without the elastomeric structure (e.g., a suction cup). In one embodiment, the wire leads are made of nickel-plated copper or aluminum. In some embodiments, the wire leads are attached via welding, soldering, or brazing. In some embodiments, the wire leads are attached to the outer dimension of the electrode. According to an embodiment of the invention, a gold electrode is plated on the bottom surface of the support ring.

Figure 20:
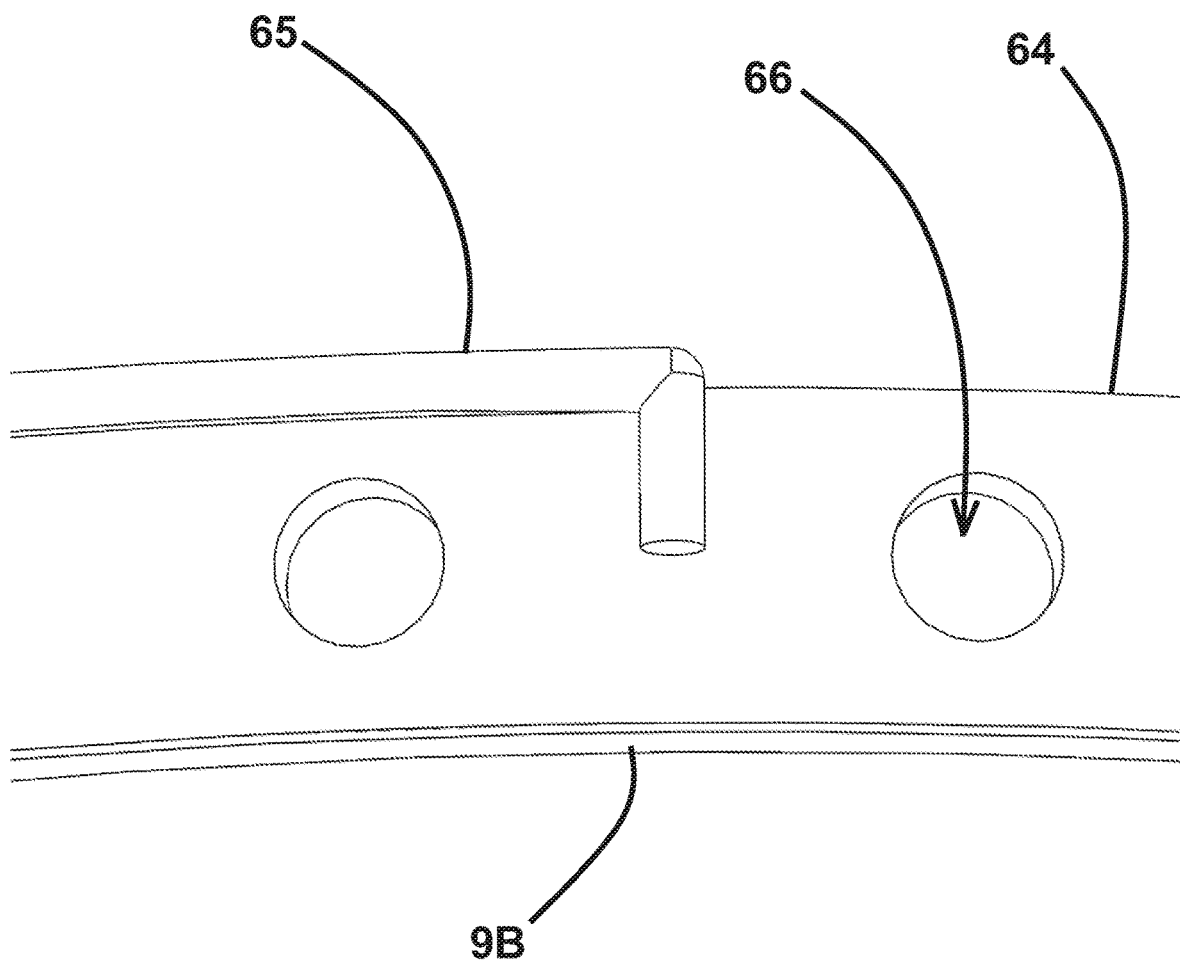
FIG. 20 is an expanded view of the attachment of the wire lead to the electrode support ring, according to an embodiment of the invention.

FIG. 20 shows an expanded view of the attachment of the wire lead to the electrode support ring, according to an embodiment of the invention. Holes or openings in the support ring 66 allow for suction flow and/or locking into the suction cup by potting material, and also help to avoid kinking in the electrode when expanding from a compressed state. In this design, the current will flow from the lead into the ring. It will then flow through both the gold electrode and the elastic ring. Because gold is about 34 times more conductive than nitinol or stainless steel, the current density in the gold will be 34 times greater than in the ring. Since Power=$I^2R$ (where I is current, and R is resistance), the power density in the gold is much greater than in the ring, so the gold will heat up enough to cut the capsule membrane, while the ring will not heat up enough to cause outgassing of the elastomer (e.g., silicone, or polyurethane) to become a concern. Any of the devices described herein could include the design of FIGS. 19 and 20.

Figure 21:
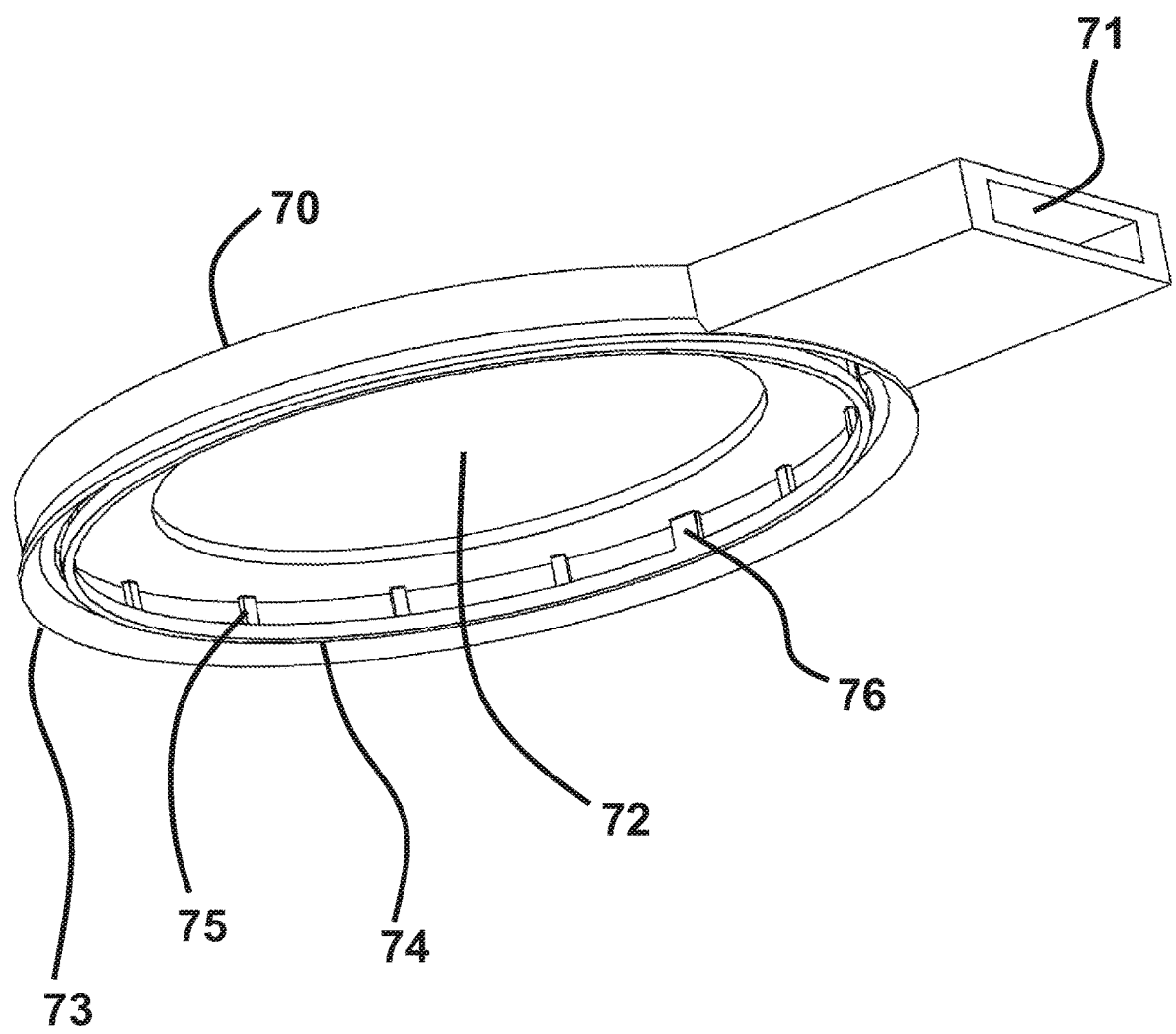
FIG. 21 shows an elastomeric structure connected to an electrode via an electrode support structure, according to an embodiment of the invention.
Figure 22:
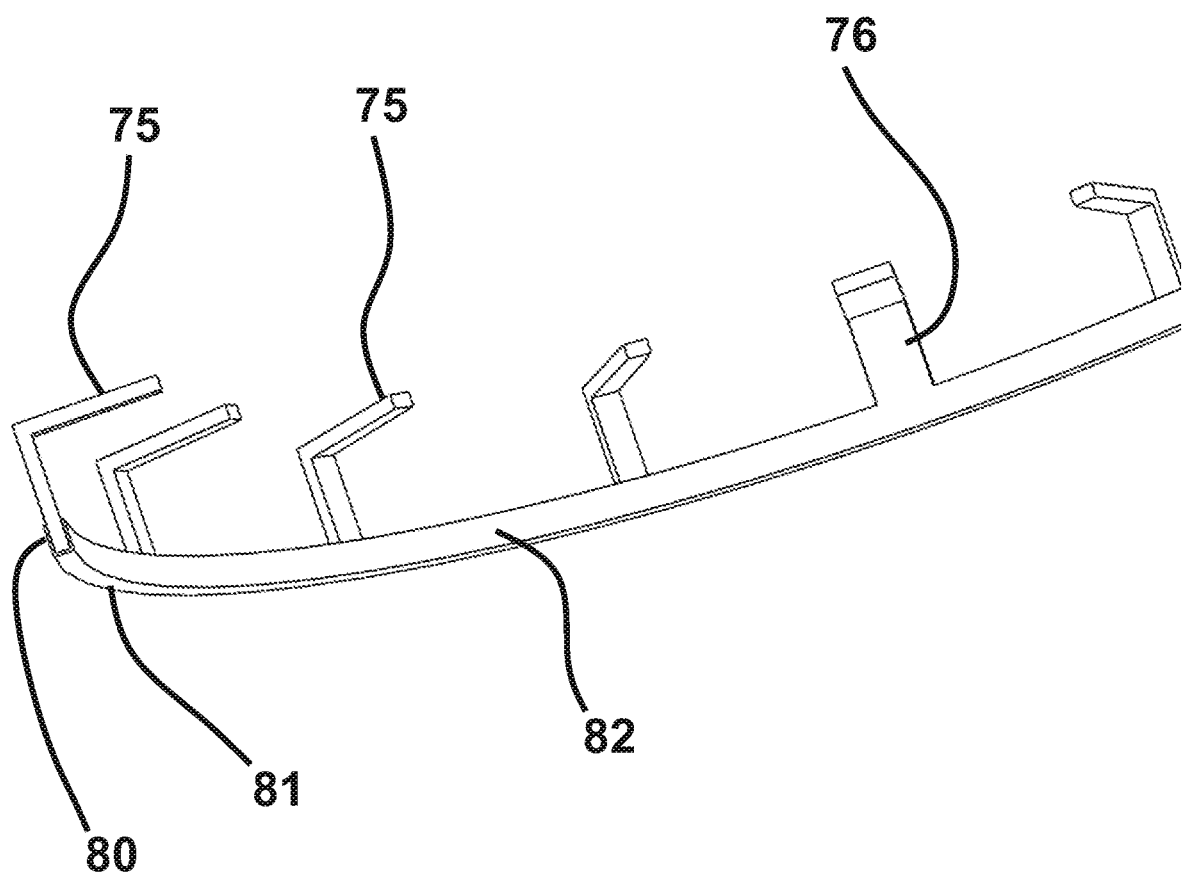
FIG. 22 is an expanded view of the interface between an electrode and electrode support structure comprising tabs, according to an embodiment of the invention.

FIGS. 21-24 show an embodiment of the invention in which the elastic support for the electrode isolates the elastomeric structure (e.g., a suction cup) from current running through the electrode by having discrete tabs 75. In one embodiment, these discrete tabs act as the electrode support structure. The tabs decrease the heat flow to the elastomeric structure by preventing current leakage from the electrode. In one embodiment, the support structure and electrode are continuous, with tabs cut out of the top portion connected to the elastomeric structure, preventing current from flowing in a circuit around the top of the support structure. The bottom of the support structure has no cutouts, and thus can act as a cutting element (e.g., an electrode) with current flowing in a continuous path around the cutting element and generating the necessary heating for capsule cutting. In this case, a cutout is any modification to the support structure that inhibits current flow around the portion of the support structure attached to the elastomeric structure. These cutouts may result in 'tabs' that can be pointed radially into the center of the elastomeric structure (as shown in FIGS. 21-24), or can be aligned circumferentially (e.g., pointing in a direction that generally follows the circumference of the elastomeric structure, see FIG. 25 as an example), or can be otherwise positioned. These tabs can also be shorter or longer than those shown in FIGS. 21-24 (e.g., the portion of the tab extending into the elastomeric structure could be shortened). FIG. 21 shows an elastomeric structure 70, having a compliant sealing skirt 73, and a neck with a lumen 71. The gold electrode 74 and gold lead 76 are supported by the superelastic nitinol structure, which is potted in the elastomeric structure. Gold plating may be applied to the inner dimension 82, and/or bottom 81, and/or outer dimension 80 surfaces as needed (FIG. 22). In one embodiment, the surface 72 adheres to the excised membrane patch so that it will be removed from the eye along with the device.

Figure 23:
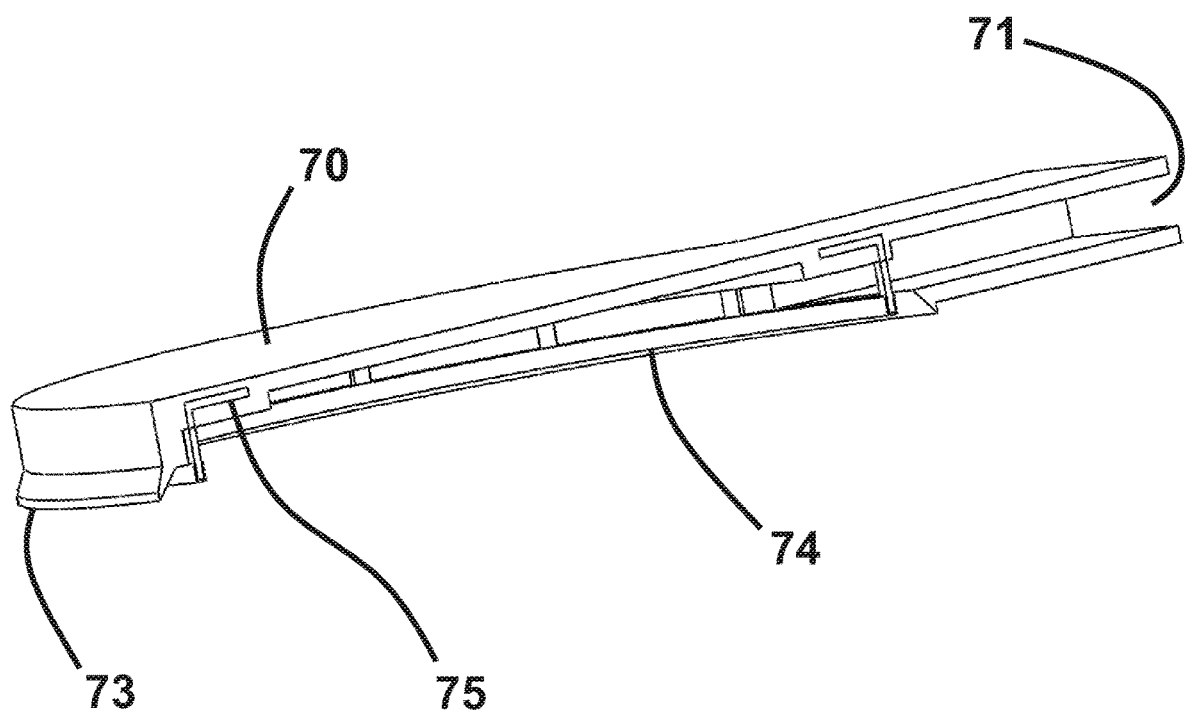
FIG. 23 shows the interface between the electrode support structure and the elastomeric structure (e.g., suction cup) via bent tabs located within the elastomeric structure, according to an embodiment of the invention.
Figure 24:
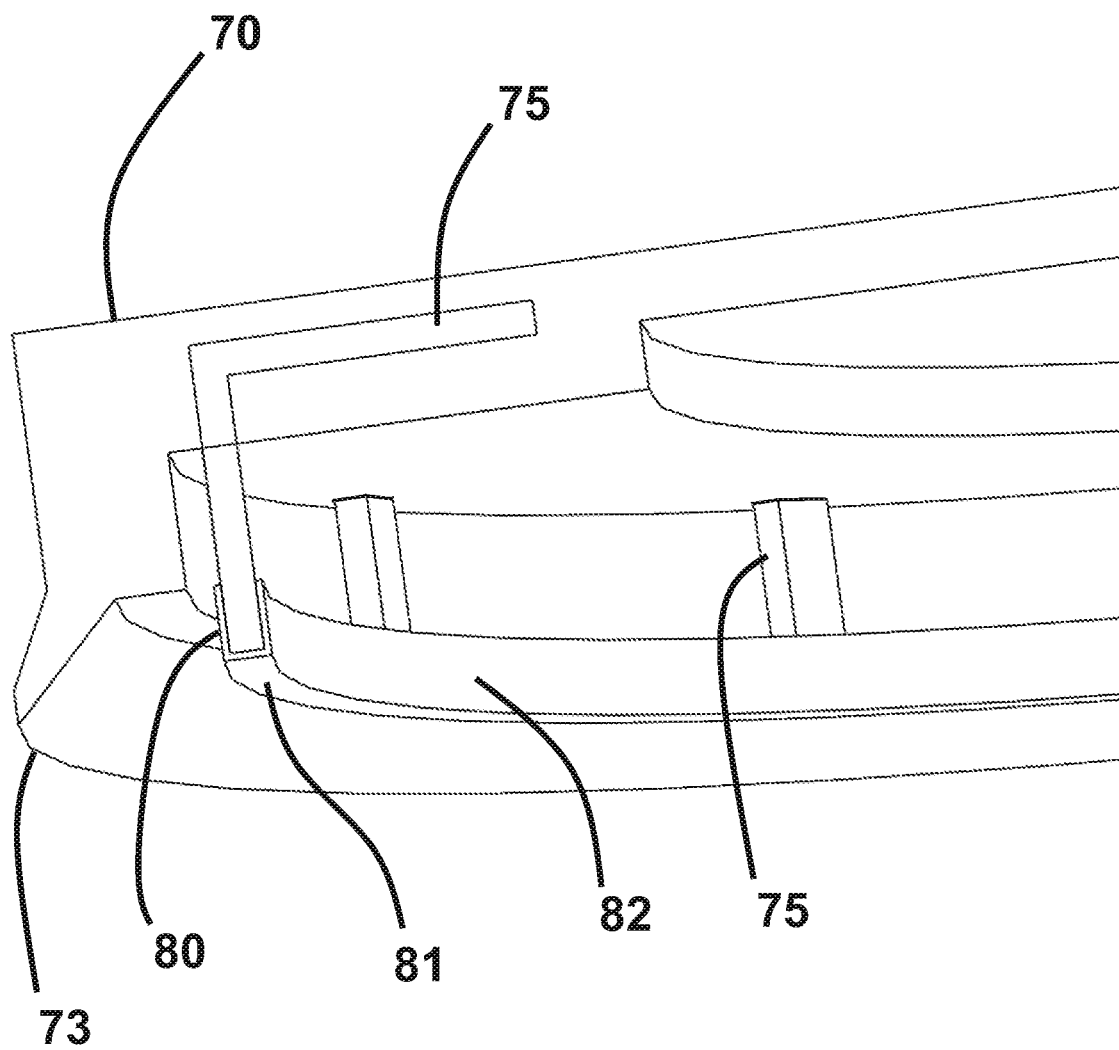
FIG. 24 is an expanded side view of the interface between the electrode support structure and the elastomeric structure (e.g., suction cup) via bent tabs inserted into the elastomeric structure, according to an embodiment of the invention.

In one embodiment, the electrode comprises vertical members. The narrowness of these vertical members prevents heat conduction from traveling up the electrode support structure comprised of several tabs 75 (FIG. 22). The attachment of this electrode to the suction cup is shown in FIG. 23, according to an embodiment of the invention. In some embodiments, a complete circuit is only present on the bottom of the electrode support structure around the electrode, preventing electrons from flowing up the support structure into the elastomeric structure (e.g., the suction cup). In one embodiment, the tabs 75 are essentially rigid compared to the silicone. In some embodiments, the tabs are made from stainless steel or superelastic nitinol.

Figure 25:
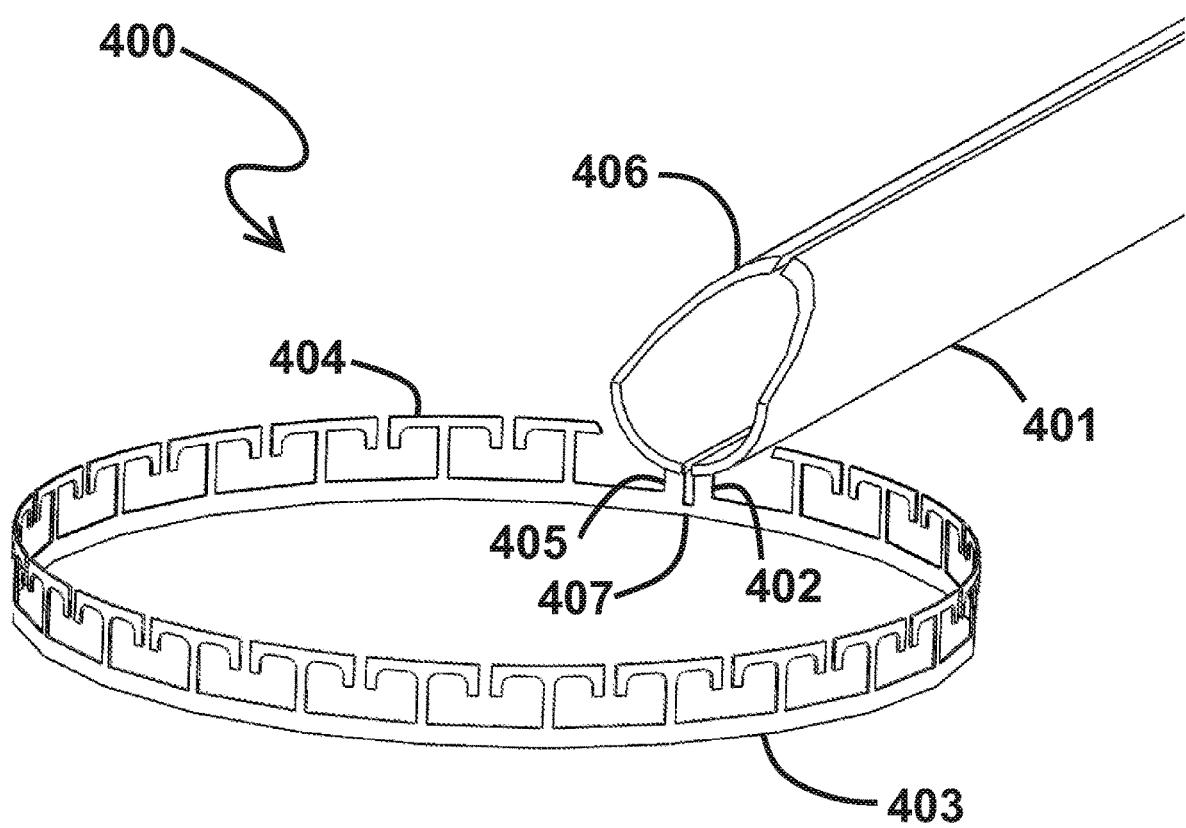
FIG. 25 is a top perspective view of another design of the support structure and cutting element, according to an embodiment of the invention

FIG. 25 is a top perspective view of another design of the support structure and cutting element 400, according to an embodiment of the invention. In use, current can flow from rigid lead 401 through connecting lead 402 and into electrode ring 403. The current can proceed around electrode ring 403 (i.e., the cutting element), through connecting lead 405 to rigid lead 406. Optional ligament 407 is designed to vaporize at the beginning of the pulse, so that it will not be present to conduct current during the remainder of the pulse. Anchoring tabs 404 are also shown in FIG. 25. In one embodiment, the cutting element is a circular cutting element mounted to the underside of the suction cup with the anchoring tabs 404 (i.e., the support structure). In some embodiments, the tabs may have different shapes to attach to the suction cup, for example bent tabs 75 as shown in FIG. 22. In this embodiment, the support structure provides both a supporting function and its edge provides the cutting function (i.e., one structure serves both functions). The top portion of the support structure (where it is in contact with the elastomeric structure) has cutouts that prevent the current from flowing in a circuit around the top of the support structure. The bottom of the support structure has no cutouts, and thus can act as a cutting element (e.g., an electrode) with current flowing in a continuous path around the cutting element and generating the necessary heating for capsule cutting. In this case, a cutout is any modification to the support structure that inhibits current flow around the portion of the support structure attached to the elastomeric structure. These cutouts may result in 'tabs' that can be pointed radially into the center of the elastomeric structure (e.g., FIGS. 21-24), or can be aligned circumferentially (e.g., FIG. 25). In certain embodiments, the cutting element can take other shapes (e.g., elliptical, square, rectangular, irregular, and other shapes) for different types of surgical procedures where a differently shaped incision in the tissue is desired. Similarly, the suction cup can take on other shapes, as well.

Cutting Mechanism

Cutting of the capsular membrane is thought to occur as follows. The suction force stretches the membrane over the electrode. This puts the membrane in tension exactly on the circle where cutting is desired. The applied forces are acting to pull the material inside the circle away from the adjoining material outside the circle, but the membrane is too strong to break from this force alone. When the electrical discharge heats up the electrode, heat starts to flow into the membrane, water, and visco that may be trapped between the electrode and membrane. As the temperature of the region of the membrane close to the electrode increases, the membrane material loses its mechanical strength. The membrane is held together by hydrogen bonds, Van der Waals forces, mechanically intertwined molecular chains, and covalent bonds. As the temperature increases the bonds break in order of increasing strength: Van der Waals, hydrogen bonds, mechanical entanglement, then covalent bonds. Even before covalent bonds break, the heated region is approaching a state of being locally melted, and if the number of covalent bonds holding the membrane intact is low, the tensile and shear stresses may be high enough to break the membrane. At the same time, water in the region is becoming heated above the boiling point so the pressure within the membrane is increasing. The weakening of the membrane, the local high expansive pressure from steam within the membrane, and the far field applied tensile and shear stresses are all acting to break the membrane on the circle defined by the electrode. Additional pressure is applied by any steam or expanding visco that is trapped between the membrane and the electrode. After the membrane breaks, the "melted" edges will re-solidify as new hydrogen bonds are formed on cool down. This will make the new edge smooth and free from stress concentrating defects. In one embodiment, the fast cutting mechanism of the microsurgery/capsulotomy device works well due to its speed. It allows cutting to take place before the heat from the energy discharge has diffused more than about 25 microns, confining the energy used for the cut within the volume of membrane where bond breaking is needed. After cutting is complete, the heat diffuses away in three dimensions, however, the heat is only about 0.1 joules, so gross temperature rise of the tissue does occur. There is not enough time or energy for material diffusion or coagulation of large molecules to occur.

The fact that the adult capsule tears in shear as neatly as it does, shows that there is little or no covalent cross-linking between molecules in-plane. Molecules can slide past each other vertically, and with this type of bonding increased temperature weakens it so it will tear at lower applied stress. Pediatric capsules are tougher so they may have more in-plane cross-linking, and this may require a different design for the electrode. Looking at the electrode designs in FIG. 3C, different distributions of shear and tensile stress can be achieved, and the magnitudes of particular stresses can be controlled by the suction pressure, and the energy and duration of the electrical discharge. Note that as the mechanical suction force is increased, the thermal energy component can be decreased. It will not be necessary to generate steam expansion if the suction force alone is great enough to make the molecules slide past each other in the microscopic melt zone. Therefore, the maximum temperature of the electrode may be reduced.

As currently practiced, the cataract operation is done with the anterior chamber filled with "viscoelastic material". A viscoelastic material is one that behaves as an elastic solid on short time scales, and flows as a viscous liquid on long time scales. Therefore the suction force may be greatly increased if it was timed as a short pulse to coincide with the electrical discharge. The mechanical motion of the capsule membrane at the electrode can be small (e.g., 0.005 mm to 0.05 mm). Suction force is limited by cavitation, but cavitation takes time to develop, and the timing of the pulse is too short (e.g., <0.010 second). Therefore, according to one embodiment of the invention, the sequence in use would be:

1. Apply low-level suction to establish the seal of the suction cup against the lens.
2. Start the high suction pulse (the mechanical pulse will be slower than the electrical discharge).
3. At the peak of suction, discharge the electrical pulse.
4. Turn off the suction pulse.

In one embodiment, high suction pulse is generated by having the lumen of the stem filled by a piston that can be rapidly moved away from the suction cup. It does not need to move far (e.g., 0.05 mm to 1 mm if it has a large cross section). The design should maximize the orifice area leading to the interior of the suction cup. In one embodiment, a piston occupies the stem and an extension (e.g., 1.5 mm wide, 0.1 mm thick) from this piston located above the electrode support ring reaches into the suction cup (during compression of the suction cup to enter the corneal incision, the piston is withdrawn up into the stem). This extension also has a vacuum channel and orifice to capture the excised membrane patch.

Figure 26:
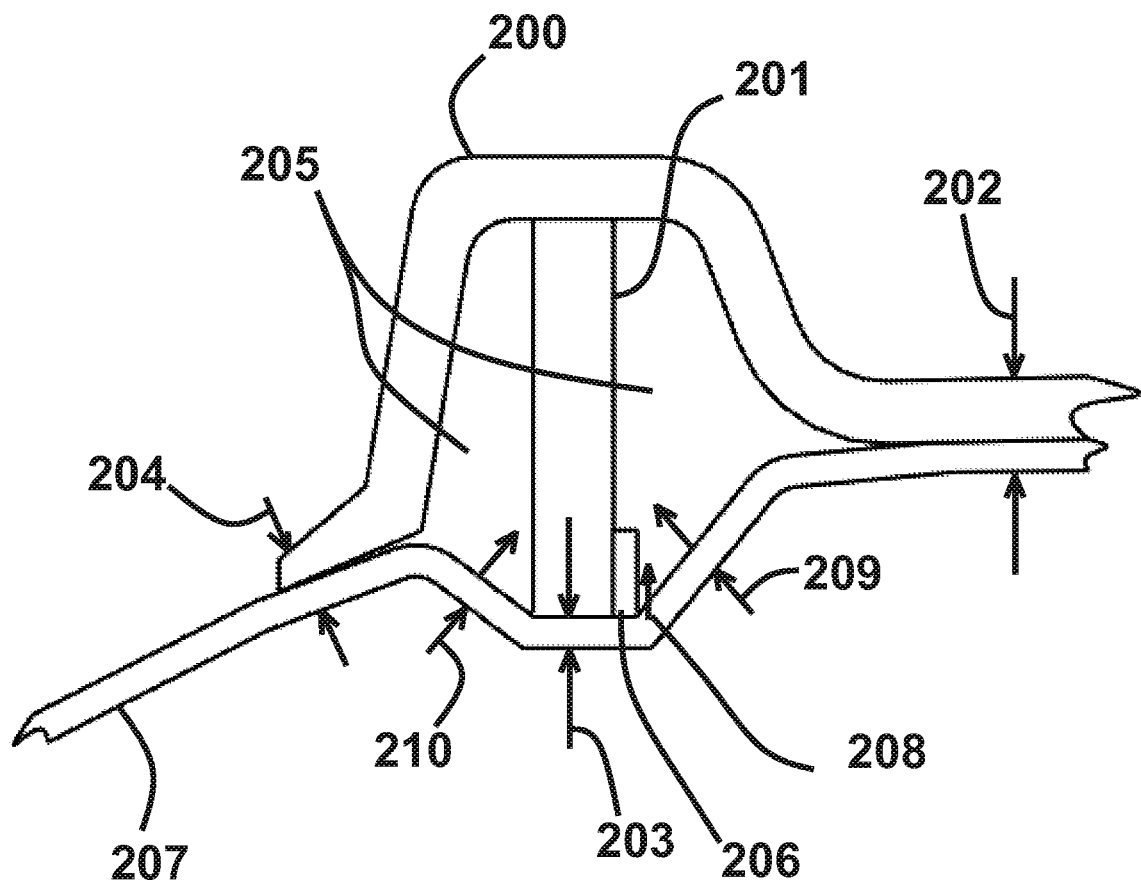
FIG. 26 shows a schematic cross-section of the applied forces in the vicinity of an electrode, according to an embodiment of the invention.

FIG. 26 shows a schematic cross section of the applied forces in the vicinity of an electrode. Suction forces on the OD and ID sides of the electrode clamp the membrane in place against the bottom of the elastic support ring. Shear forces are maximized at the corners, so the electrode is located at a corner (in this case the ID corner) and when heat weakens the membrane there, the cutting process occurs. Low-pressure regions 205 cause the higher ambient pressure to create forces 209 and 210 acting on the membrane (207), and create clamping areas 202, 203, 204 to immobilize the membrane. When electrode 206 is heated by an electrical discharge, shear force 208 breaks the membrane where it becomes weakened by thermal breaking of bonds. Suction cup 200 simply serves to separate low-pressure regions 205 from the ambient pressure of the surrounding fluid environment.

Figure 27:
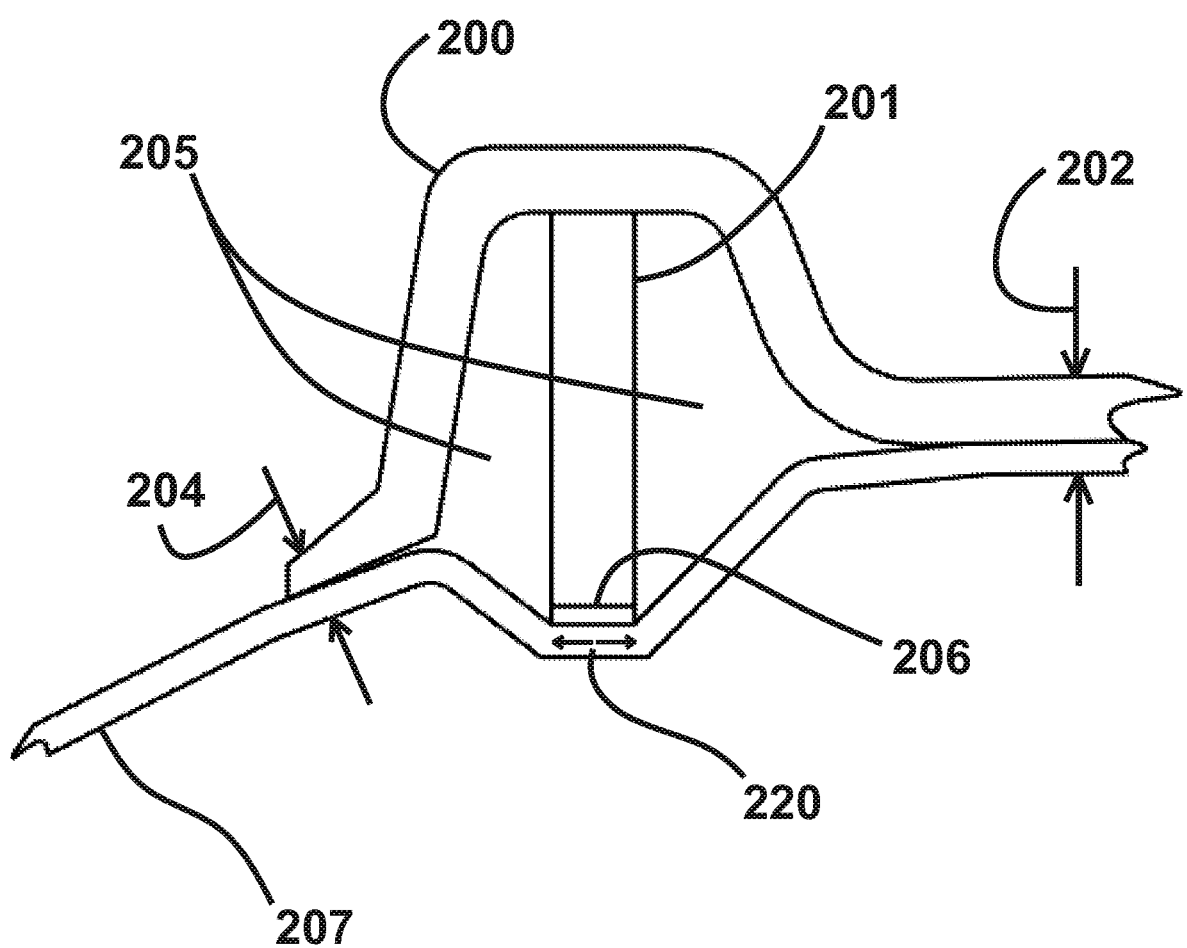
FIG. 27 shows a schematic cross-section with the electrode located on the bottom surface of the elastic support ring, according to an embodiment of the invention.

For pediatric cases, where the membrane does not tear properly with shear forces alone, it may help to use a design that will increase the tensile stress. FIG. 27 shows a schematic cross section with the electrode (208) located on the bottom surface of the elastic support ring (201). The static stress field set up in the membrane at that location will be more tensile (220). Then when the electrical discharge occurs, it can be made to have more energy and achieve a higher temperature to generate more expansive steam pressure within the membrane than would be needed for the adult capsulotomy to provide cutting. The forces shown in FIGS. 26 and 27 can apply to any of the devices described herein.

Alternative Suction Channel Embodiments

Figure 28:
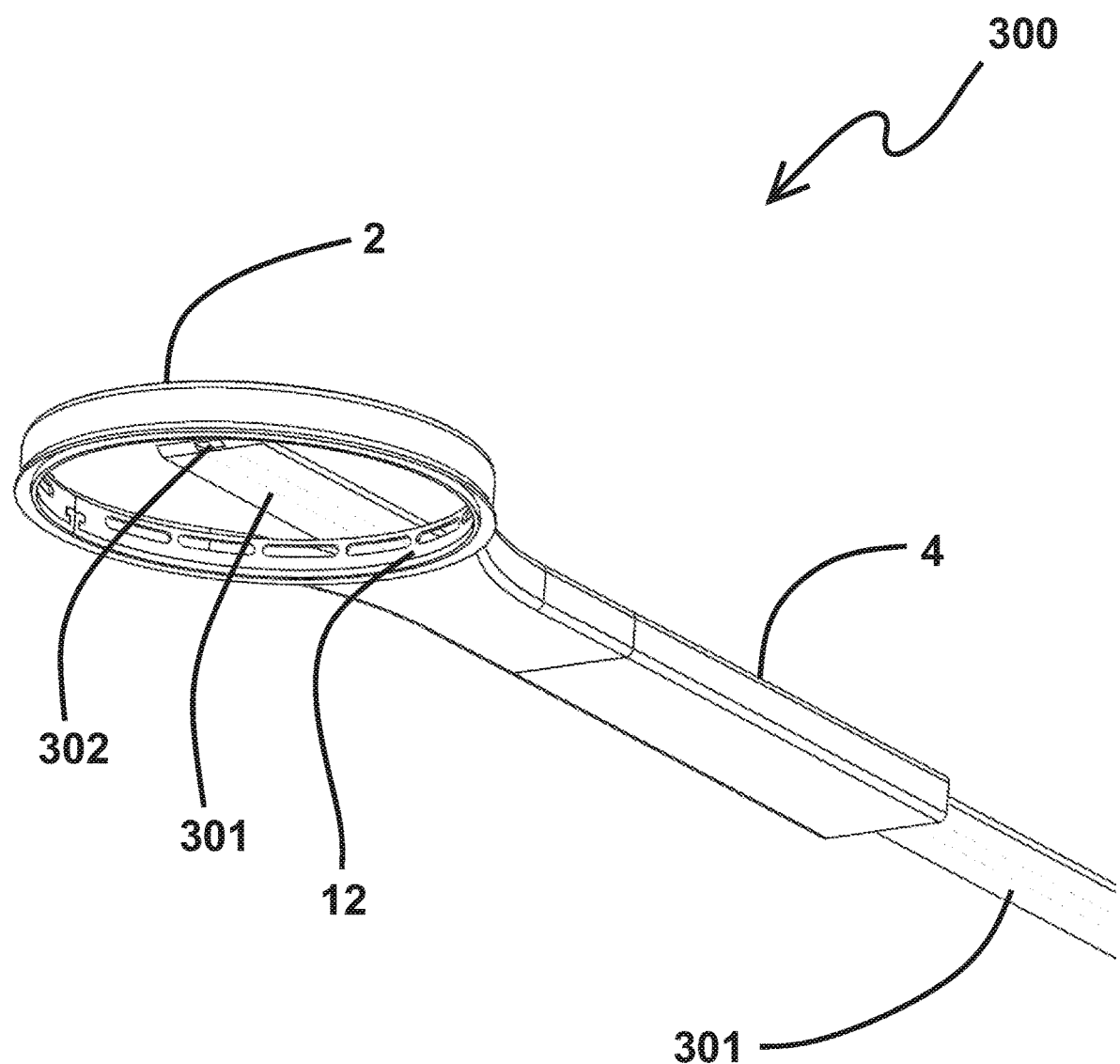
FIG. 28 shows an embodiment of the microsurgery/capsulotomy device with a deployed piston for applying suction to the suction cup.
Figure 29:
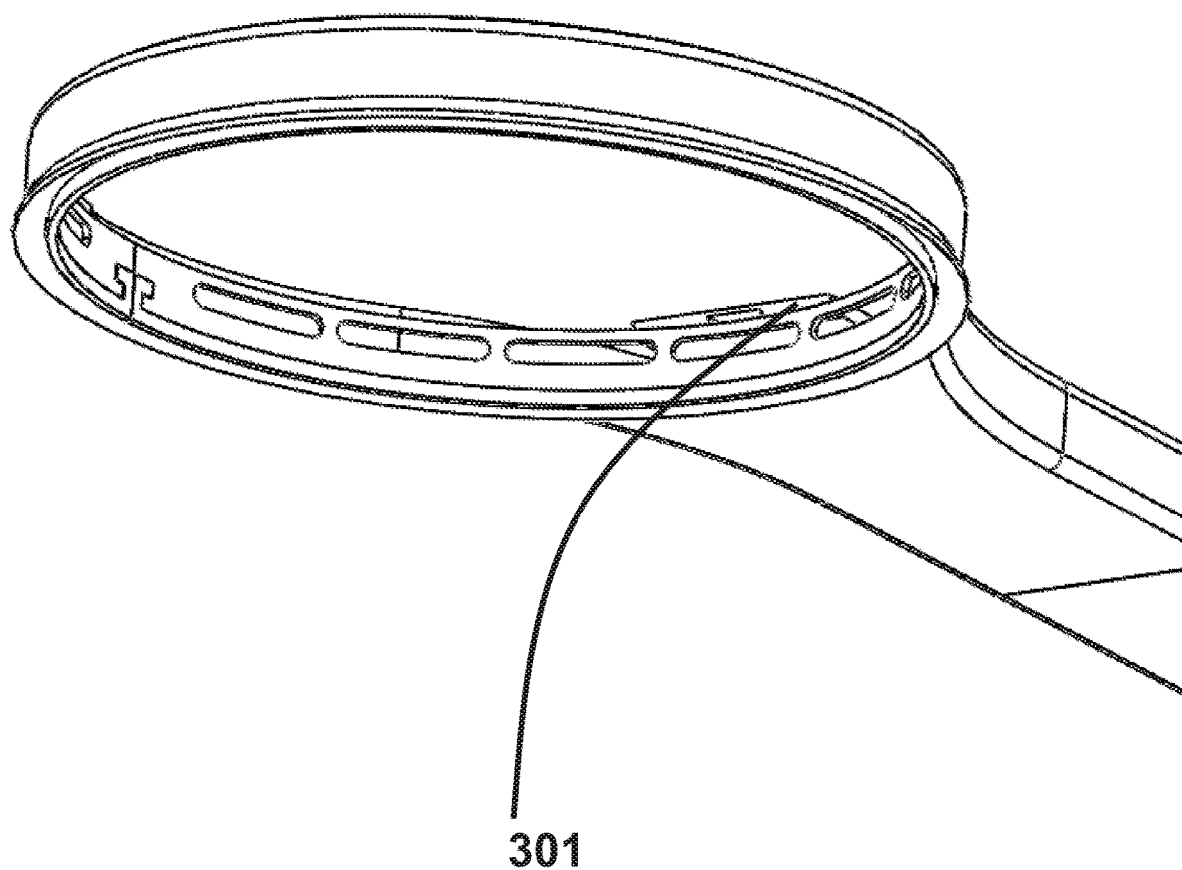
FIG. 29 shows an embodiment of the microsurgery/capsulotomy device with a piston for applying suction to the suction cup where the piston is retracted into the stem of the device.

Looking at device 300 in FIGS. 28 and 29, piston 301 can be deployed all the way across the interior of the suction cup 2 (or part way if desired). It has a suction channel 302 that is plumbed independently of the main suction in the stem 4 with its own source of vacuum. The piston 301 slides over the electrode support ring 12. FIG. 29 shows the piston in its retracted position, as it would be during the compression of the suction cup to enter the eye. Once in the eye, the piston would be pushed across the suction cup (FIG. 28). To create a pulse of suction, the piston would be rapidly withdrawn to its retracted position (FIG. 29) thereby reducing the volume inside the suction cup. Such motion would not be done manually, but by a spring, or solenoid, or other mechanism. Then the piston would be moved back towards the center of the suction cup to capture the excised membrane by suction. Then the main suction channel would go in reverse to put material into the suction cup to release its hold on the lens.

The above description is included to illustrate the operation of the embodiments and is not meant to limit the scope of the invention. The scope of the invention is to be limited only by the following claims. From the above discussion, many variations will be apparent to one skilled in the relevant art that would yet be encompassed by the spirit and scope of the invention. As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

We claim:

1. A device for accessing a lens capsule through a cornea of an eye, the device comprising:
   an elastomeric structure;
   a support structure mounted to the elastomeric structure, the support structure comprising a plurality of openings and a plurality of tabs; and
   a cutting element extending from the support structure that is mounted to the elastomeric structure, wherein the cutting element and the elastomeric structure are not in physical contact.

2. The device of claim 1, wherein the cutting element is an electrode, and the device comprises one or more electrical elements for delivering current to an electrical lead capsule.

3. The device of claim 2, wherein the electrode is circular.

4. The device of claim 2, wherein the electrode comprises a continuous element and the device further comprises a first and second connecting trace connecting the electrical lead to the electrode, wherein the first and second connecting traces are positioned on opposite sides of the electrode to allow current to travel in two opposite directions for conducting current uniformly around the portion of the tissue to be severed.

5. The device of claim 1, wherein the elastomeric structure is a suction cup.

6. The device of claim 5, further comprising one or more suction elements connected to the suction cup for applying suction within the suction cup.

7. The device of claim 5, wherein the suction cup further comprises a flared skirt extending from an edge of the suction cup for securing the suction cup against the lens capsule to form a vacuum seal.

8. The device of claim 1, wherein a portion of the support structure in contact with the elastomeric structure does not form a complete circuit for current flow.

9. The device of claim 1, wherein the cutting element is positioned on one side of the support structure.

10. The device of claim 1, wherein the cutting element is positioned on at least two sides of the support structure.

11. The device of claim 10, wherein the cutting element comprises at least two electrodes.

12. A device for excising a tissue, the device comprising:
   a housing;
   a suction cup that can be configured in a compressed position and a decompressed position;
   a compression element exposed from the housing and that can configure the suction cup between the compressed position to the decompressed position;
   a first suction channel in the housing and coupled to the suction cup, the first suction channel configured to provide suction to the suction cup; and
   a piston forming a second suction channel and coupled to the suction cup, the second suction channel operably independent from the first suction channel, the piston configured to capture an excised portion of the tissue.

13. The device of claim 12, further comprising a support structure mounted to the suction cup.

14. The device of claim 13, further comprising a cutting element that can be configured in a compressed position and a decompressed position and extending from the support structure.

15. The device of claim 14, wherein the support structure and the cutting element are continuous and made from the same material.

16. The device of claim 13, wherein the support structure comprises at least two materials, wherein a first material of the at least two materials is more conductive than a second material of the at least two materials.

17. The device of claim 16, wherein the first material of the at least two materials is located along a bottom edge of the support structure.

18. The device of claim 12, wherein the suction cup further comprises a flared skirt extending from an edge of the suction cup for securing the suction cup against the tissue to form a vacuum seal.

19. The device of claim 12, further comprising a stem of the housing attached to the suction cup to provide support between a handle and the suction cup.

* * * * *

UNITED STATES PATENT AND TRADEMARK OFFICE
CERTIFICATE OF CORRECTION

PATENT NO. : 11,426,308 B2
APPLICATION NO. : 16/917682
DATED : August 30, 2022
INVENTOR(S) : Christopher Guild Keller It is certified that error appears in the above-identified patent and that said Letters Patent is hereby corrected as shown below:

In the Claims

In Column 21, Claim 2, Line 15, delete "an electrical lead capsule" and insert --the electrode--.

Signed and Sealed this
Fifteenth Day of November, 2022

Katherine Kelly Vidal
*Director of the United States Patent and Trademark Office*